United States Patent
Holland et al.

(10) Patent No.: US 11,754,575 B2
(45) Date of Patent: Sep. 12, 2023

(54) CORE CALIBRATION OF ANALYZERS

(71) Applicant: Beckman Coulter, Inc., Brea, CA (US)

(72) Inventors: Mark Holland, Little Canada, MN (US); Conan Dewitt, Eagan, MN (US)

(73) Assignee: BECKMAN COULTER, INC., Brea, CA (US)

( * ) Notice: Subject to any disclaimer, the term of this patent is extended or adjusted under 35 U.S.C. 154(b) by 1148 days.

(21) Appl. No.: 16/314,261

(22) PCT Filed: Jun. 30, 2017

(86) PCT No.: PCT/US2017/040244
§ 371 (c)(1),
(2) Date: Dec. 28, 2018

(87) PCT Pub. No.: WO2018/005945
PCT Pub. Date: Jan. 4, 2018

(65) Prior Publication Data
US 2019/0162739 A1 May 30, 2019

Related U.S. Application Data

(60) Provisional application No. 62/357,090, filed on Jun. 30, 2016.

(51) Int. Cl.
*G01N 35/00* (2006.01)
*G16B 40/00* (2019.01)
*C12Q 1/6851* (2018.01)

(52) U.S. Cl.
CPC ..... *G01N 35/00693* (2013.01); *C12Q 1/6851* (2013.01); *G16B 40/00* (2019.02); *G01N 2035/00653* (2013.01); *G01N 2035/00702* (2013.01); *G01N 2035/00881* (2013.01)

(58) Field of Classification Search
CPC . G01N 35/00693; G16B 40/00; C12Q 1/6851
See application file for complete search history.

(56) References Cited

U.S. PATENT DOCUMENTS

| | | | |
|---|---|---|---|
| 5,257,212 A | 10/1993 | Kildal-Brandt et al. | |
| 5,424,212 A | 6/1995 | Pinsl-Ober et al. | |
| 5,616,504 A | 4/1997 | Brown et al. | |
| 6,825,041 B2 | 11/2004 | Qureshi et al. | |
| 2015/0141284 A1* | 5/2015 | Smith | G01N 33/505 506/10 |
| 2016/0097785 A1 | 4/2016 | Horstmann et al. | |

FOREIGN PATENT DOCUMENTS

| | | |
|---|---|---|
| CN | 1644163 | 7/2005 |
| CN | 105510249 | 4/2016 |
| EP | 2273404 A1 | 1/2011 |
| WO | WO 1994/019689 A1 | 9/1994 |
| WO | WO 2012/012779 A2 | 1/2012 |

OTHER PUBLICATIONS

Chinese Office Action dated Mar. 18, 2022 for Application No. 201780041098.7, 10 pages.
Gelman Andrew, et. al., Bayesian Analysis of Serial Dilution Assays, Biometrics 60, pp. 407-417, Jun. 2004.
Giltinan, David M and Davidian, Marie, Assays for Recombinant Proteins: a Problem in Non-Linear Calibration, Statistics in Medicine, vol. 13, pp. 1165-1179 (1994), John Wiley & Sons, Ltd.
Unadkat, Jashvant D., et. at., Bayesian Calibration, Analytica Chimica Acta, 181, pp. 27-36, (1986) Elsevier Science Publishers B.V.
Fong, Y., et. al., A Robust Bayesian Random Effects Model for Nonlinear Calibration Problems, Biometrics 68, pp. 1103-1112, Dec. 2012, The International Biometric Society.
Racine-Poon, Amy, A Bayesian Approach to Nonlinear Calibration Problems, Journal of the American Statistical Association, vol. 83, No. 403, pp. 650-656, Sep. 1988.
Fridley Brooke L., et al., A Bayesian hierarchical nonlinear model for assessing the association between genetic variation and drug cytotoxicity, Statistics in Medicine, Statist. Med. 2009; 28, pp. 2709-2722, Jul. 2009, Wiley InterScience.
International Search Report and Written Opinion for International Application No. PCT/US2017/040244, 10 pages.
International Preliminary Report on Patentability dated Jan. 1, 2019 for International Application No. PCT/US2017/040244, 7 pages.
Sivaganesan, Mano, et al. "A Bayesian method for calculating real-time quantitative PCR calibration curves using absolute plasmid DNA standards." BMC bioinfoimatics 9.1 (2008): 120.
Sivaganesan, Mano, et al. "Improved strategies and optimization of calibration models for real-time PCR absolute quantification." Water Research 44.16 (2010): 4726-4735.
Sivaganesan, Mano, et al. "MPN estimation of qPCR target sequence recoveries from whole cell calibrator samples." Journal of microbiological methods 87.3 (2011): 343-349.
European Examination Report dated Jan. 23, 2020 for Application No. EP 17743418.0, 6 pgs.

\* cited by examiner

*Primary Examiner* — Jerry Lin
(74) *Attorney, Agent, or Firm* — Frost Brown Todd LLP

(57) ABSTRACT

Methods and systems for determining a dose of an analyte in an unknown sample on an instrument, such as a nucleic acid analyzer, immunoassay analyzer, or clinical chemistry analyzer using a reagent from a selected assay lot are described. The methods and systems use core dose-response information based on measurements of response values to a set of calibrators on a plurality of other instruments and assay lot-specific response information to calibrate the instrument.

39 Claims, 10 Drawing Sheets

CORE CALIBRATION OF ANALYZERS

This application is a National Stage Entry of PCT Application No. PCT/US17/40244, entitled "Core Calibration of Analyzers," filed Jun. 30, 2017, which claims priority to U.S. Provisional Application No. 62/357,090, entitled "Core Calibration of Analyzers," filed Jun. 30, 2016, the disclosures of which are incorporated by reference herein.

TECHNICAL FIELD

The present disclosure is generally directed to calibration techniques for analyzers using ligand binding analysis to detect the presence or dose of an analyte, and more particularly to calibration techniques for immunoassay systems, clinical chemistry systems, and nucleic acid systems. The present disclosure is also directed to such systems having the capability to analyze samples in a manner that is calibrated using such techniques. The present disclosure is further directed to calibration analysis systems and methods for producing information needed in such analysis.

BACKGROUND

Immunoassay instruments measure the concentration of a molecule in a solution through the use of an antibody or other ligand capable of binding the molecule. The molecule being detected is referred to as an "analyte". The analyte is often a protein or protein fragment, but may be a small molecule such as a drug, a vitamin, or other biologic compound. The analyte is detected when it, a part of it, or an analog of it, binds with a ligand in an assay, creating a reaction product which then produces a measurable signal, e.g., an optically or electrically detectable change in the assay that the instrument measures. A general description of some immunoassay instruments can be found in U.S. Pat. No. 6,825,041 to Qureshi et al., assigned to Beckman Coulter, Inc. Similar to immunoassay instruments, clinical chemistry instruments also measure the concentration of an analyte in a solution through the use of a ligand capable of binding the analyte. The analyte is detected when it, a part of it, or an analog of it, binds with a ligand in an assay, creating a reaction product which then produces a measurable signal; e.g., an optically or electrically detectable change in the assay that the instrument measures.

The presence of a nucleic acid in a biological fluid can be detected or measured using a nucleic acid system. In this case, the particular nucleic acid being detected is the analyte and a complementary nucleic acid is the ligand. Various techniques for analysis, such as polymerase chain reaction ("PCR"), can be employed in the detection, e.g., using an array or cartridge containing reagents used in an assay with a variety of reagents used to detect different nucleic acids. An example nucleic acid instrument is described in WO2012/012779 to Wilson et al., assigned to Beckman Coulter, Inc.

Immunoassay instruments, clinical chemistry instruments, and nucleic acid instruments work together with related assay reagents (including ligands) to form analyzer systems. The signals produced by analyzer systems are generally indirect measurements of the analytes correlated to signals from known analyte concentration(s) through a calibration process. The ligands and other assay reagents used in an assay vary between manufacturing lots, and the signals detected by an instrument for a given analyte concentration can vary when different lots of assay reagents are used for the measurements.

Calibration is performed using calibration samples that contain the analyte at a known concentration. The instrument measures a response signal for each processed calibration sample; this signal is mapped to the known concentration associated with the particular calibration sample. In some cases, a mathematical or graphical model of the instrument's response to the calibration samples of different concentrations of the analyte may be created. Such a mapping is variously known as a dose-response curve, a standard curve, or a calibration curve.

Samples with an unknown concentration of analyte (test samples) may then be processed with the calibrated instrument. The response signal from test samples may be combined with the previously-established calibration curve or the model to determine the unknown analyte concentrations in each test sample.

An analyzer may be calibrated by running a series of calibration samples of known concentration of an analyte on an individual analyzer. The number of such samples run to perform such calibration effectively on the individual analyzer is typically fairly large, e.g. at least six samples per analyte. The results from the analyzer on the known concentration samples are then modeled, e.g., by doing a least-squares curve fit of the instrument responses in relation to the known concentrations of the calibration samples. This curve is then used on the analyzer where the calibration is performed to estimate the amount of an analyte present in unknown samples processed on the analyzer.

Variation in the individual calibration curves may occur, even when repeating identical calibration samples on a single instrument. This calibration to calibration variance can have a significant impact on assay precision and quality control. Individual calibrations can be influenced by "noisy data," such as variation in the measurements of calibration samples, or outlier data points generated by anomalies in sample processing. If the noisy data is sufficient to trigger curve failure mechanisms in the calibration software, then excessive failure rates in instrument calibration can occur. Even if the noisy data is not sufficient to trigger curve failure limits, the effect of the noise can affect assay precision and quality control (QC) recovery. Sources of noise include inherent variation in the performance of the analyzer, environmental factors, and variation in the reagents used to perform the analysis.

Production of a calibration curve on an instrument is expensive; it requires dedication of a slice of instrument time and an aliquot of assay reagents for each replicate of each calibrator tested. Calibration also requires distribution of calibrators to the instrument and frequently needs operator interaction to set up and review. Calibration curve measurements, like any other measurements, are susceptible to noise that may be reduced by averaging (or otherwise combining) measurements from multiple repetitions. However such repetition requires even more instrument time, reagents, and expense. Calibration at a central location, such as an instrument supplier location or a customer location, can reduce some of the local costs but does not account for variations among instruments and, to some extent, merely shifts costs between locations. A calibration curve may also change for each assay reagent manufacturing lot "assay lot"); production of a factory calibration curve for each assay lot multiplies the frequency, expense, and complexity of calibration. Running a factory calibration curve followed by a reduced set of calibrators or adjusters on a fielded instrument to modify the collected data. (or the factory calibration curve) reduces the burden on individual instruments but can make the dose response calculation reliant on one or a few relatively noisy data points.

Thus there is a need for a method of assay calibration that is lot-insensitive but allows good assay performance on fielded analyzers without undue burden on instrument operation.

SUMMARY

One example embodiment of the present disclosure described herein includes an example procedure for determining a dose of an analyte in an unknown sample on an instrument using a reagent from a selected assay lot. The example procedure may be performed using a computer processor or using multiple processors working together or in communication with each other. The example procedure includes receiving core dose-response information based on measurements of response values to a set of calibrators on a plurality of other instruments. The example procedure also includes receiving information based on measurements of response values of one or more calibration adjusters on the instrument using the selected assay lot. The example procedure further includes receiving measurements of the unknown sample made on the instrument using the selected assay lot, and determining the dose of the analyte in the unknown sample based on the core dose-response information, the information based on measurements of response values of one or more calibration adjusters, and the measurements of the unknown sample.

In one variant of the above example procedure, the procedure further optionally includes receiving a core dose-response curve defined by a model including a plurality of parameter estimates, where the plurality of parameter estimates fit the model to the response values of the set of calibrators, where each dose-response curve model parameter estimate is associated with at least one of a plurality of probability densities, and where each probability density is a combination of an assay lot-specific density contribution and an instrument-specific density contribution, and determining the dose of the analyte in the unknown sample is further based, at least in part, on the core dose-response curve.

Another example embodiment of the present disclosure described herein includes an example procedure for generating a dose-response model for an instrument configured to determine an analyte with a selected assay lot. The example procedure includes measuring response values to a calibrator using a plurality of source instruments and a plurality of source assay lots. The example procedure also includes generating a core dose-response curve defined by a model including a model parameter, Where the core dose-response curve includes a parameter estimate of the model parameter that fits the model to the response values of the calibrator, where the parameter estimate is associated with a probability density, and where the probability density is a combination of a lot-specific density contribution and an instrument-specific density contribution. The example procedure also includes measuring a response value of a calibration adjuster on the instrument using the selected assay lot. The example procedure further includes calculating a dose-response curve using the model, the parameter estimate, the probability densities and the response value of the calibration adjuster, where the instrument is not one of the plurality of source instruments. The step of calculating the dose response curve may include applying Bayesian inference using the probability distributions as a prior distribution and the response value of the calibration adjuster as evidence to form a posterior distribution. The method may also include assigning a central measure of the posterior distribution as the value of the model parameter. The central measure may be one of a median, a mode, or a mean of the posterior distribution. The plurality of source assay lots may not include the selected assay lot.

Yet another example embodiment of the present disclosure described herein includes an example procedure for determining a dose of an analyte in an unknown sample on an instrument using a selected assay lot. The example procedure includes measuring response values to a set of calibrators using a plurality of source instruments and a plurality of source assay lots. The example procedure also includes generating a core dose-response curve defined by a model including a plurality of parameter estimates, where the plurality of parameter estimates fit the model to the response values of the set of calibrators, where each core dose-response curve model parameter estimate is associated with at least one of a plurality of probability densities, and where each probability density is a combination of a lot-specific density contribution and an instrument-specific density contribution. The example procedure further includes transmitting the plurality of parameter estimates and the plurality of probability densities to the instrument. The example procedure moreover includes measuring response values of one or more calibration adjusters on the instrument using the selected assay lot. The example procedure additionally includes generating an instrument-specific, selected lot-specific dose-response curve using the model, the transmitted plurality of parameter estimates, the transmitted plurality of probability densities, and the response values of the one or more calibration adjusters. The example procedure also includes measuring a response of the unknown sample on the selected instrument using the selected assay lot. The example procedure further includes determining the dose of the unknown sample from the measured response using the instrument-specific, selected lot-specific dose-response curve. The step of calculating the dose response curve may include applying Bayesian inference using the plurality of probability distributions as prior distributions and the response values of the one or more calibration adjuster as evidence to form a plurality of posterior distributions, with one posterior distribution associated with each model parameter. The method may also include assigning a central measure of each posterior distribution as the value of the associated model parameter. The central measure may be one of a median, a mode, or a mean of the posterior distribution. The plurality of source assay lots may not include the selected assay lot.

Yet another example embodiment of the present disclosure described herein includes an example procedure for determining a dose of an analyte in an unknown sample. The example procedure includes measuring response values of a set of calibrators using a plurality of source instruments and a plurality of source assay lots. The example procedure includes generating a core dose-response curve defined by a model, a plurality of model parameters, and a plurality of probability densities, where the plurality of model parameters fit the model to the response values of the set of calibrators, where each model parameter is associated with at least one of the plurality of probability densities, and where each probability density of the plurality of probability densities is a combination of a lot-specific density contribution and an instrument-specific density contribution. The example procedure includes calculating an address to a stored representation of parametric adjustments, where the address indirectly addresses parametric adjustments corresponding to the plurality of parameter estimates and the plurality of probability densities. The example procedure includes selecting an instrument and an assay lot, where the selected instrument is not one of the plurality of source instruments. The example procedure includes transmitting the plurality of parameter estimates and the pointer to the selected instrument. The example procedure includes measuring response values of one or more calibration adjusters on the selected instrument using the selected assay lot. The example procedure includes generating an instrument-specific, lot-specific dose-response curve using the model, the plurality of parameter estimates, values accessed from a replicate of the stored representation of parametric adjustments addressed by the address, and the response values of the one or more calibration adjusters as measured on the selected instrument using the selected lot. The example procedure includes measuring response value of the unknown sample on the selected instrument using the selected assay lot. The example procedure includes determining the dose of the unknown sample from the measured response using the instrument-specific, lot-specific dose-response curve.

In the above example procedures, it will be appreciated that the selected assay lot may be different than the plurality of source assay lots, although in other alternatives, it may be one of the source assay lots.

In the above example procedures, the model used may be a four-parameter logistic model and the probability density of at least one of the plurality of model parameters may include the sum of a lot-specific density contribution and an instrument-specific density contribution. Optionally, the probability density of at least one of the plurality of model parameters includes a logarithm of a sum of a lot-specific density contribution and an instrument-specific density contribution. Optionally, the probability density of the at least one of the plurality of model parameters further includes a correlated lot x instrument contribution. Optionally, the plurality of model parameters may include parameters a, b, c, and d and wherein the probability density associated with each of model parameters a, c, and d includes a logarithm of a sum of a respective lot-specific density contribution and a respective instrument-specific density contribution. The probability density associated with model parameters b may include the sum of a parameter b lot-specific density contribution and a parameter b instrument-specific density contribution.

More particularly, in the four parameter logistic model in the above procedures: the model may have the form $$f(x) = \frac{a_{ij} - d_{ij}}{1 + \exp\{b_{ij}(\ln(x) - \ln(c_{ij}))\}} + d_{ij}$$

where x denotes dose, f(x) denotes response value associated with dose x, where a, b, c, and d denote the model parameters, and where index i denotes instruments and index j denotes reagent lots. This four-parameter logistic model may conform to the following properties:

$$\ln(a_{ij} - d_{ij}) = \alpha_0 + \alpha_{Lot_j} + \alpha_{Instrument_i} + \alpha_{Lot \times Instrument_{ij}}$$

$$b_{ij} = \beta_0 + \beta_{Lot_j} + \beta_{Instrument_i} + \beta_{Lot \times Instrument_{ij}}$$

$$\ln(c_{ij}) = \gamma_0 + \gamma_{Lot_j} + \gamma_{Instrument_i} + \gamma_{Lot \times Instrument_{ij}}$$

$$\ln(d_{ij}) = \xi_0 + \xi_{Lot_j} + \xi_{Instrument_i} + \xi_{Lot \times Instrument_{ij}}$$

where $\alpha$, $\beta$, $\gamma$, and $\xi$ each denote contributions to the respective parameters a, b, c, and d.

It will further be appreciated that a five parameter logistic model or other model may also be used in place of the four parameter logistic model in the above example procedures.

In the above example procedures, generating a core dose-response curve may include calculating a prior distribution using a stochastic method. The stochastic method may include a Markov Chain Monte Carlo method, or other Monte Carlo type model. Alternatively, generating an instrument-specific, lot-specific dose-response curve may be performed using a deterministic method, e.g., a numerical integration method, such as Gaussian quadrature.

It will be further appreciated in all of the above example procedures that the instrument and the plurality of source instruments use ligand binding analysis to determine the dose of the analyte present in a sample. The instrument and the plurality of source instruments may, e.g., be immunoassay analyzers, clinical chemistry analyzers, or nucleic acid analyzers.

Another example embodiment of the present disclosure described herein includes an article of manufacture. The article of manufacture includes a tangible computer medium having instructions stored thereon. The instructions, when executed by a processor, cause the processor to perform a procedure. For each of the various procedures described above or elsewhere herein, it will be appreciated that such an article of manufacture having instructions causing a computer processor to carry out steps of the procedure may be provided.

Another example embodiment of the present disclosure described herein includes an example instrument, e.g., an instrument using ligand binding analysis such as a nucleic acid analyzer, immunoassay analyzer, or clinical chemistry analyzer. The instrument may be configured to use the calibration procedures above to better analyze the dose of analytes in samples. The example instrument includes a measurement device to measure response information of an analyte using a reagent from an assay lot, including detectors and related equipment that are found in nucleic acid analyzers, immunoassay analyzers, or clinical chemistry analyzers. The example instrument includes a processor in communication with the measurement device. The processor is configured, e.g., under software control, to receive core dose-response information based on measurements of response values to a set of calibrators on a plurality of other instruments. The processor can be controlled by an instrument supplier or by a customer. The processor can be physically located at an instrument supplier's location or at a customer's location. Alternatively, the processor can be located at a remote computer server is not physically located at an instrument supplier's location or at a customer's location. For example, the remote computer server can be cloud computing, also known as on-demand computing. The processor is further configured to receive information based on measurements of response values of one or more calibration adjusters on the instrument using the assay lot and receive information based on measurements of response values of one or more calibration adjusters on the instrument using the assay lot. The processor is further configured to receive measurements of the unknown sample made on the instrument using the assay lot. The processor is further configured to determine the dose of the unknown sample from the measured response based on the core dose-response information, the information based on measurements of response values of one or more calibration adjusters, and the measurements of the unknown sample. Optionally, the processor may be further configured to receive a core dose-response curve defined by a model including a plurality of parameter estimates, wherein the plurality of parameter estimates fit the model to the response values of the set of calibrators, wherein each core dose-response model parameter estimate is associated with at least one of a plurality of probability densities, and wherein each probability density is a combination of a lot-specific density contribution and an instrument-specific density contribution, and determine the dose of the unknown sample based at least in part on the core dose-response curve.

Aspects of the subject matter described herein may be useful alone or in combination with one or more other aspect described herein. Without limiting the foregoing description, in a first aspect of the present disclosure, a method of generating a dose-response curve for an instrument configured to determine an analyte with a selected assay lot includes measuring response values to one or more calibrators using a plurality of source instruments and a plurality of assay lots and generating a core dose-response curve defined by a model including a model parameter, wherein the core dose-response curve includes at least one parameter estimate of the model parameter that fits the model to the response values of the one or more calibrators, wherein the parameter estimate is associated with at least one probability density, and wherein the probability density is a combination of a lot-specific density contribution and an instrument-specific density contribution. The example method also includes receiving, from the instrument, measured response values of one or more calibration adjusters on the instrument using the selected assay lot, and generating an instrument-specific, lot-specific dose-response curve using the model, the at least one parameter estimate, the at least one probability density, and the measured response values of the one or more calibration adjusters. The example method further includes transmitting the instrument-specific, lot-specific dose-response curve to the instrument.

In accordance with a second aspect of the present disclosure, which may be used in combination with any other aspect listed herein unless stated otherwise, the step of generating the instrument-specific, lot-specific dose-response curve includes applying Bayesian inference using the probability estimate as a prior distribution and the measured response values of the one or more calibration adjusters to form a posterior distribution, and assigning a central measure of the posterior distribution as the value of the model parameter.

In accordance with a third aspect of the present disclosure, which may be used in combination with any other aspect listed herein unless stated otherwise, the central measure is one of a median, a mode, or a mean.

In accordance with a fourth aspect of the present disclosure, which may be used in combination with any other aspect listed herein unless stated otherwise, the step of generating a core dose-response curve includes calculating a prior distribution using a stochastic method.

In accordance with a fifth aspect of the present disclosure, which may be used in combination with any other aspect listed herein unless stated otherwise, the stochastic method includes a Markov Chain Monte Carlo method.

In accordance with a sixth aspect of the present disclosure, which may be used in combination with any other aspect listed herein unless stated otherwise, the step of generating the instrument-specific, lot-specific dose-response curve includes a deterministic method.

In accordance with a seventh aspect of the present disclosure, which may be used in combination with any other aspect listed herein unless stated otherwise, the deterministic method includes a numerical integration method.

In accordance with an eighth aspect of the present disclosure, which may be used in combination with any other aspect listed herein unless stated otherwise, the numerical integration method includes Gaussian quadrature integration.

In accordance with a ninth aspect of the present disclosure, which may be used in combination with any other aspect listed herein unless stated otherwise, a method for determining a dose of an analyte in an unknown sample on an instrument using a reagent from a selected assay lot includes receiving, at a computer processor, a core dose-response curve defined by a model including at least one parameter estimate, wherein each parameter estimate is associated with at least one probability density, and wherein each probability density is a combination of a lot-specific density contribution and an instrument-specific density contribution. The example method also includes receiving, at the computer processor, information on measurements of response values of one or more calibration adjusters on the instrument using the selected assay lot, and receiving, at a computer processor, an instrument-specific, selected lot-specific dose-response curve using the model, the transmitted plurality of parameter estimates, the transmitted plurality of probability densities, and the response values of the one or more calibration adjusters. The example method further includes receiving, at the computer processor, measurements of the unknown sample made on the instrument using the selected assay lot, and determining, at the computer processor, the dose of the analyte in the unknown sample using the instrument-specific, selected lot-specific dose-response curve and the measurements of the unknown sample.

In accordance with a tenth aspect of the present disclosure, which may be used in combination with any other aspect listed herein unless stated otherwise, the example method further comprises receiving, from a plurality of instruments, measured response values of one or more calibration adjustors on the plurality of instruments using one or more assay lots, generating an adjusted dose-response curve using the model, the at least one parameter estimate, the at leas one probability density, and the measured response values of one or more calibration adjustors on the plurality of instruments using the one or more assay lots, and transmitting the adjusted dose-response curve to at least one instrument from the plurality of instruments.

In accordance with an eleventh aspect of the present disclosure, which may be used in combination with any other aspect listed herein unless stated otherwise, the receiving and the transmitting steps occur over an Internet connection.

In accordance with a twelfth aspect of the present disclosure, which may be used in combination with any other aspect listed herein unless stated otherwise, the model is a four-parameter logistic model and the at least one probability density includes a sum of a lot-specific density contribution and an instrument-specific density contribution.

In accordance with a thirteenth aspect of the present disclosure, which may be used in combination with any other aspect listed herein unless stated otherwise, the model is a four-parameter logistic model and the at least one probability density includes a logarithm of a sum of a lot-specific density contribution and an instrument-specific density contribution.

In accordance with a fourteenth aspect of the present disclosure, which may be used in combination with any other aspect listed herein unless stated otherwise, the four-parameter logistic model has form $$f(x) = \frac{a_{ij} - d_{ij}}{1 + \exp\{b_{ij}(\ln(x) - \ln(c_{ij}))\}} + d_{ij}$$

wherein x denotes dose, f(x) denotes response value associated with dose x, wherein a, b, c, and d denote the model parameters, and wherein index i denotes instruments and index j denotes reagent lots.

In accordance with a fifteenth aspect of the present disclosure, which may be used in combination with any other aspect listed herein unless stated otherwise, $$\ln(a_{ij} - d_{ij}) = \alpha_0 + \alpha_{Lot_j} + \alpha_{Instrument_j} + \alpha_{Lot \times Instrument_{ij}}$$

$$b_{ij} = \beta_0 + \beta_{Lot_j} + \beta_{Instrument_j} + \beta_{Lot \times Instrument_{ij}}$$

$$\ln(c_{ij}) = \gamma_0 + \gamma_{Lot_j} + \gamma_{Instrument_j} + \gamma_{Lot \times Instrument_{ij}}$$

$$\ln(d_{ij}) = \xi_0 + \xi_{Lot_j} + \xi_{Instrument_j} + \xi_{Lot \times Instrument_{ij}}$$

wherein $\alpha$, $\beta$, $\gamma$, and $\xi$ each denote contributions to the respective parameters a, b, c, and d and the respective subscripts denote the source of the contributions.

In accordance with a sixteenth aspect of the present disclosure, which may be used in combination with any other aspect listed herein unless stated otherwise, the at least one probability density further includes a correlated lot x instrument contribution.

In accordance with a seventeenth aspect of the present disclosure, which may be used in combination with any other aspect listed herein unless stated otherwise, the example method further includes a plurality of model parameters and a plurality of probability densities, wherein each model parameter is associated with a model parameter, wherein the plurality of model parameters includes parameters a, b, c, and d, and wherein the probability density associated with each of model parameters a, c, and d includes a logarithm of a sum of a respective lot-specific density contribution and a respective instrument-specific density contribution.

In accordance with an eighteenth aspect of the present disclosure, which may be used in combination with any other aspect listed herein unless stated otherwise, the probability density associated with model parameter b includes a sum of a parameter b lot-specific density contribution and a parameter b instrument-specific density contribution.

In accordance with a nineteenth aspect of the present disclosure, which may be used in combination with any other aspect listed herein unless stated otherwise, a system for determining a dose of an analyte in an unknown sample using a reagent from a selected assay lot includes a measurement device to measure response information of an analyte using a reagent from an assay lot, and a processor in communication with the measurement device. The example processor is configured to receive a core dose-response curve defined by a model including at least one parameter estimate, wherein each parameter estimate is associated with at least one probability density, and wherein each probability density is a combination of a lot-specific density contribution and an instrument-specific density contribution. The example processor is also configured to receive information based on measurements of response values of one or more calibrator adjusters on the instrument using the assay lot, and receive a measured response of the unknown sample made on the instrument using the assay lot. The example processor is further configured to determine the dose of the unknown sample an instrument-specific, selected lot-specific dose-response curve and the measured response of the unknown sample, wherein the instrument-specific, selected lot-specific dose-response curve using the model, the transmitted plurality of parameter estimates, the transmitted plurality of probability densities, and the response values of the one or more calibration adjusters.

In accordance with a twentieth aspect of the present disclosure, which may be used in combination with any other aspect listed herein unless stated otherwise, the processor is further configured to generate the instrument-specific, selected lot-specific dose-response curve based on the model, the at least parameter estimate, the at leak one probability density, and the response values of the one or more calibration adjusters.

In accordance with a twenty-first aspect of the present disclosure, which may be used in combination with any other aspect listed herein unless stated otherwise, a method for determining a dose of an analyte in an unknown sample on an instrument using a reagent from a selected assay lot includes receiving, at a computer processor, core dose-response information based on measurements of response values to a set of calibrators on a plurality of other instruments using a plurality of other assay lots, and receiving, at the computer processor, information based on measurements of response values of one or more calibration adjusters on the instrument using the selected assay lot. The example method also includes receiving, at the computer processor, measurements of the unknown sample made on the instrument using the selected assay lot, and determining, at the computer processor, the dose of the analyte in the unknown sample based on the core dose-response information, and the information based on measurements of response values of one or more calibration adjusters, and the measurements of the unknown sample.

In accordance with a twenty-second aspect of the present disclosure, which may be used in combination with any other aspect listed herein unless stated otherwise, the example method further includes receiving a core dose-response curve defined by a model including a plurality of parameters, wherein the plurality of parameters fit the model to the response values of the set of calibrators, wherein each parameter is associated with at least one of a plurality of probability densities, and wherein each probability density is a combination of an assay lot-specific density contribution and an instrument-specific density contribution, and wherein determining the dose of the analyte in the unknown sample is further based, at least in part, on the core dose-response curve.

In accordance with a twenty-third aspect of the present disclosure, which may be used in combination with any other aspect listed herein unless stated otherwise, a method of generating a dose-response model for an instrument configured to determine an analyte with a selected assay lot includes measuring response values to a calibrator using a plurality of source instruments and a plurality of source assay lots, and generating a core dose-response curve defined by a model including a model parameter, wherein the core dose-response curve includes a parameter estimate of the model parameter that fits the model to the response values of the calibrator, wherein the parameter estimate is associated with a probability density, and wherein the probability density is a combination of a lot-specific density contribution and an instrument-specific density contribution. The example method further includes measuring a response value of a calibration adjuster on the instrument using the selected assay lot, and calculating a dose-response curve using the model, the parameter estimate, the probability densities, and the response value of the calibration adjuster, wherein the instrument is not one of the plurality of source instruments.

In accordance with a twenty-fourth aspect of the present disclosure, which may be used in combination with any other aspect listed herein unless stated otherwise, the step of calculating the dose response curve includes applying Bayesian inference using a probability estimate as a prior distribution and the response value of the calibration adjuster as evidence to form a posterior distribution, and assigning a central measure of the posterior distribution as the value of the model parameter.

In accordance with a twenty-fifth aspect of the present disclosure, which may be used in combination with any other aspect listed herein unless stated otherwise, the central measure is one of a median, a mode, or a mean.

In accordance with a twenty-sixth aspect of the present disclosure, which may be used in combination with any other aspect listed herein unless stated otherwise, a method for determining a dose of an analyte in an unknown sample on an instrument using a selected assay lot includes measuring response values to a set of calibrators using a plurality of source instruments and a plurality of source assay lots, and generating a core dose-response curve defined by a model including a plurality of parameter estimates, wherein the plurality of parameter estimates fit the model to the response values of the set of calibrators, wherein each parameter estimate is associated with at least one probability density, and wherein each probability density is a combination of a lot-specific density contribution and an instrument-specific density contribution. The example method also includes transmitting the plurality of parameter estimates and the plurality of probability densities to the instrument, and measuring response values of one or more calibration adjusters on the instrument using the selected assay lot. The example method further includes generating an instrument-specific, selected lot-specific dose-response curve using the model, the transmitted plurality of parameter estimates, the transmitted plurality of probability densities, and the response values of the one or more calibration adjusters. The example method moreover includes measuring a response of the unknown sample on the selected instrument using the selected assay lot, and determining the dose of the unknown sample from the measured response using the instrument-specific, selected lot-specific dose-response curve.

In accordance with a twenty-seventh aspect of the present disclosure, which may be used in combination with any other aspect listed herein unless stated otherwise, a method for determining a dose of an analyte in an unknown sample includes measuring response values of a set of calibrators using a plurality of source instruments and a plurality of source assay lots, and generating a core dose-response curve defined by a model, a plurality of model parameters, and a plurality of probability densities, wherein the plurality of model parameters fit the model to the response values of the set of calibrators, wherein each model parameter is associated with at least one of the plurality of probability densities, and wherein each probability density of the plurality of probability densities is a combination of a lot-specific density contribution and an instrument-specific density contribution. The example method also includes calculating an address to a stored representation of parametric adjustments, wherein the address indirectly addresses parametric adjustments corresponding to the plurality of parameter estimates and the plurality of probability densities, and selecting an instrument and an assay lot, wherein the selected instrument is not one of the plurality of source instruments. The example method further includes transmitting the plurality of parameter estimates and the pointer to the selected instrument, measuring response values of one or more calibration adjusters on the selected instrument using the selected assay lot, and generating an instrument-specific, lot-specific dose-response curve using the model, the plurality of parameter estimates, values accessed from a replicate of the stored representation of parametric adjustments addressed by the address, and the response values of the one or more calibration adjusters as measured on the selected instrument using the selected lot. The example method additionally includes measuring response value of the unknown sample on the selected instrument using the selected assay lot, and determining the dose of the unknown sample from the measured response using the instrument-specific, lot-specific dose-response curve.

In accordance with a twenty-eighth aspect of the present disclosure, which may be used in combination with any other aspect listed herein unless stated otherwise, the selected assay lot is not one of the plurality of source assay lots.

In accordance with a twenty-ninth aspect of the present disclosure, which may be used in combination with any other aspect listed herein unless stated otherwise, the model is a four-parameter logistic model and the probability density of at least one of the plurality of model parameters includes the sum of a lot-specific density contribution and an instrument-specific density contribution.

In accordance with a thirtieth aspect of the present disclosure, which may be used in combination with any other aspect listed herein unless stated otherwise, the model is a four-parameter logistic model and the probability density of at least one of the plurality of model parameters includes the logarithm of the sum of a lot-specific density contribution and an instrument-specific density contribution.

In accordance with a thirty-first aspect of the present disclosure, which may be used in combination with any other aspect listed herein unless stated otherwise, the probability density of the at least one of the plurality of model parameters further includes a correlated lot x instrument contribution.

In accordance with a thirty-second aspect of the present disclosure, which may be used in combination with any other aspect listed herein unless stated otherwise, the plurality of model parameters includes parameters a, b, c, and d, and wherein the probability density associated with each of model parameters a, c, and d includes a logarithm of a sum of a respective lot-specific density contribution and a respective instrument-specific density contribution.

In accordance with a thirty-third aspect of the present disclosure, which may be used in combination with any other aspect listed herein unless stated otherwise, the probability density associated with model parameters b includes the sum of a parameter b lot-specific density contribution and a parameter b instrument-specific density contribution.

In accordance with a thirty-fourth aspect of the present disclosure, which may be used in combination with any other aspect listed herein unless stated otherwise, the four-parameter logistic model has form $$f(x) = \frac{a_{ij} - d_{ij}}{1 + \exp\{b_{ij}(\ln(x) - \ln(c_{ij}))\}} + d_{ij}$$

wherein x denotes dose, f(x) denotes response value associated with dose x, wherein a, b, c, and d denote the model parameters, and wherein index i denotes instruments and index j denotes reagent lots.

In accordance with a thirty-fifth aspect of the present disclosure, which may be used in combination with any other aspect listed herein unless stated otherwise, $$\ln(a_{ij}-d_{ij})=\alpha_0+\alpha_{Lot_j}+\alpha_{Instrument_i}+\alpha_{Lot \times Instrument_{ij}}$$

$$b_{ij}=\beta_0+\beta_{Lot_j}+\beta_{Instrument_i}+\beta_{Lot \times Instrument_{ij}}$$

$$\ln(c_{ij})=\gamma_0+\gamma_{Lot_j}+\gamma_{Instrument_i}+\gamma_{Lot \times Instrument_{ij}}$$

$$\ln(d_{ij})=\xi_0+\xi_{Lot_j}+\xi_{Instrument_i}+\xi_{Lot \times Instrument_{ij}}$$

wherein $\alpha$, $\beta$, $\gamma$, and $\xi$ each denote contributions to the respective parameters a, b, c, and d and the respective subscripts denote the source of the contributions.

In accordance with a thirty-sixth aspect of the present disclosure, which may be used in combination with any other aspect listed herein unless stated otherwise, the step of generating a core dose-response curve includes calculating a prior distribution using a stochastic method.

In accordance with a thirty-seventh aspect of the present disclosure, which may be used in combination with any other aspect listed herein unless stated otherwise, the stochastic method includes a Markov Chain Monte Carlo method.

In accordance with a thirty-eighth aspect of the present disclosure, which may be used in combination with any other aspect listed herein unless stated otherwise, the step of generating an instrument-specific, lot-specific dose-response curve includes a deterministic method.

In accordance with a thirty-ninth aspect of the present disclosure, which may be used in combination with any other aspect listed herein unless stated otherwise, the deterministic method includes a numerical integration method.

In accordance with a fortieth aspect of the present disclosure, which may be used in combination with any other aspect listed herein unless stated otherwise, the numerical integration method includes Gaussian quadrature integration.

In accordance with a forty-first aspect of the present disclosure, which may be used in combination with any other aspect listed herein unless stated otherwise, the instrument and the plurality of source instruments use ligand binding analysis to determine the dose of the analyte.

In accordance with a forty-second aspect of the present disclosure, which may be used in combination with any other aspect listed herein unless stated otherwise, the instrument and the plurality of source instruments are immunoassay analyzers.

In accordance with a forty-third aspect of the present disclosure, which may be used in combination with any other aspect listed herein unless stated otherwise, the instrument and the plurality of source instruments are nucleic acid analyzers.

In accordance with a forty-fourth aspect of the present disclosure, which may be used in combination with any other aspect listed herein unless stated otherwise, an article of manufacture comprising a tangible computer medium having stored thereon instructions which when executed by a processor, cause the processor to determine a dose of an analyte in an unknown sample on an instrument using a reagent from a selected assay lot, by receiving core dose-response information based on measurements of response values to a set of calibrators on a plurality of other instruments, receiving information based on measurements of response values of one or more calibration adjusters on the instrument using the selected assay lot, receiving measurements of the unknown sample made on the instrument using the selected assay lot, and determining the dose of the analyte in the unknown sample based on the core dose-response information, the information based on measurements of response values of one or more calibration adjusters, and the measurements of the unknown sample.

In accordance with a forty-fifth aspect of the present disclosure, which may be used in combination with any other aspect listed herein unless stated otherwise, the instructions further cause the processor to receive a core dose-response curve defined by a model including a plurality of parameter estimates, wherein the plurality of parameter estimates fit the model to the response values of the set of calibrators, wherein each core dose-response curve model parameter estimate is associated with at least one of a plurality of probability densities, and wherein each probability density is a combination of a lot-specific density contribution and an instrument-specific density contribution, and wherein determining the dose of the analyte in the unknown sample from the measured response is further based, at least in part, on the core dose-response curve.

In accordance with a forty-sixth aspect of the present disclosure, which may be used in combination with any other aspect listed herein unless stated otherwise, an instrument includes a measurement device to measure response information of an analyte using a reagent from an assay lot, and a processor in communication with the measurement device. The example processor is configured to receive core dose-response information based on measurements of response values to a set of calibrators on a plurality of other instruments, receive information based on measurements of response values of one or more calibration adjusters on the instrument using the assay lot, and receive a measured response of the unknown sample made on the instrument using the assay lot. The example processor is also configured to determine the dose of the unknown sample from the measured response based on the core dose-response information and the information based on measurements of response values of one or more calibration adjusters.

In accordance with a forty-seventh aspect of the present disclosure, Which may be used in combination with any other aspect listed herein unless stated otherwise, the core dose-response information includes a core dose-response curve defined by a model including a plurality of parameter estimates, wherein the plurality of parameter estimates fit the model to the response values of the set of calibrators, wherein each core dose-response model parameter estimate is associated with at least one of a plurality of probability densities, wherein each probability density is a combination of a lot-specific density contribution and an instrument-specific density contribution, and wherein the processor determines the dose of the unknown sample based at least in part on the core dose-response curve.

In accordance with a forty-eighth aspect of the present disclosure, any of the structure and functionality illustrated and described in connection with FIGS. 1 to 10 may be used in combination with any of the structure and functionality illustrated and described in connection with any of the other of FIGS. 1 to 10, and with any one or more of the preceding aspects unless stated otherwise.

Additional features and advantages of the disclosed system, method, and apparatus are described in, and will be apparent from, the following Detailed Description and the Figures.

DETAILED DESCRIPTION

Overview

Figure 1:
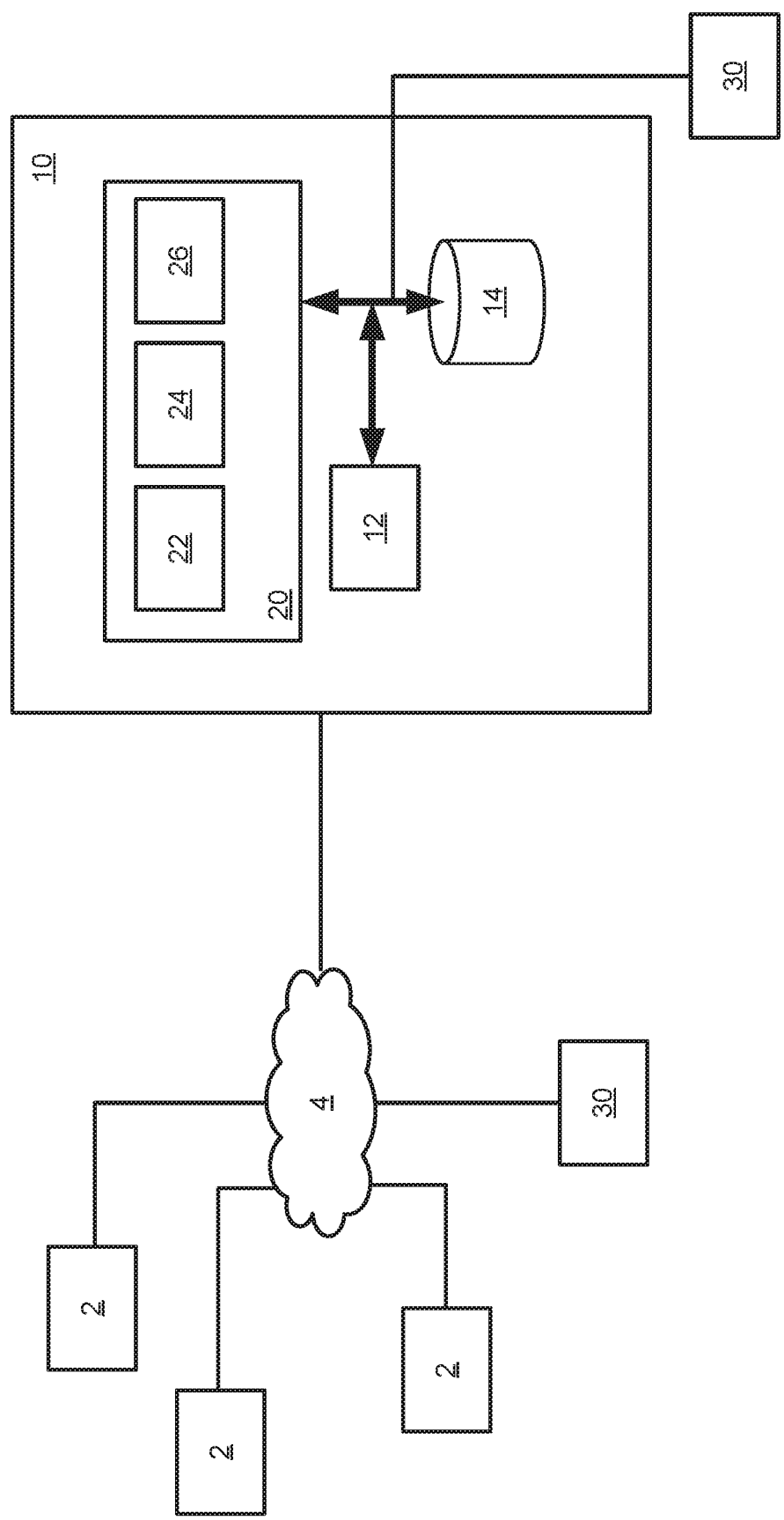
FIG. 1 illustrates an example core development tool, according to an example embodiment of the present disclosure.

Example embodiments of the present disclosure include systems for and methods of determining a concentration of an analyte using a system of a fielded instrument, assay reagents, and a source-based collection of instruments. The source-based collection of instruments generates core calibration information using multiple assay lots and then transmits that information to the fielded instrument. The fielded instrument runs a small number of calibration adjusters using a specific lot of assay reagents and combines the signals from these calibration adjusters with the received information to produce a dose-response curve useful on that instrument for that specific assay lot. The assay lots used to generate the core calibration information need not include the specific assay lot used on the fielded instrument.

The instruments, including those at the source and those fielded, form a population with a distribution of responses even to non-varying assay materials. Similarly, the assay lots, including those used to establish the core calibration information and those fielded, form a population with a distribution of responses even to non-varying calibrators on a single instrument. The differences between individual instruments and individual assay lots are real; they are not merely the result of noisy individual data points sampled from the populations.

The system uses one of several possible parametric models of the assay response, and selects appropriate values of parameters used in the model using Bayesian inference. Bayesian inference is a statistical technique that modifies a probability distribution based on new data. It enables combination of information (such as the fielded instrument response to calibration adjusters) with prior knowledge of the probability distribution of the same parameters (such as that developed from the core calibration process) to return a new estimate of the probability distribution of the parameter values. The fielded instrument then selects a value for each parameter (such as the mean or median of the probability distribution of parameter values) and uses the completed model to calculate sample results from measured sample response signals.

Core Calibration

Core Calibration Curve

A fielded instrument may be calibrated using core calibration. While "source" is used in the present disclosure for convenience, "source" is not intended to limit the geographical location of particular instruments used for core calibration, but rather to refer to a collection of instruments operated by the instrument or reagent manufacturer, which may well be located in their manufacturing facility, but may also include instruments at product development sites, clinical testing centers, research sites, or other locations of the manufacturer, partners, or customers. In core calibration, a large quantity of calibration samples, typically more than are used in individual analyzer calibration, e.g., n 6, are processed on multiple different analyzers of the same type. Typically, each source instrument runs multiple replicates of each calibration sample to reduce the influence of noise on the measurement. The results from these calibration runs on different instruments can be used to create a model of instrument response, a core calibration curve. In some embodiments, the core calibration curve may be updated as each reagent lot is manufactured. This may in some situations improve calibration reliability or reduce lot-to-lot variability.

The core curve may be constructed using multiple lots of reagents measured on multiple source instruments so that each calibrator is associated with a plurality of response values corresponding to measurements of each instrument using each lot. In general, there will be differences between the response signals for a given calibrator between instruments even with the same reagent lot and between reagent lots even on the same instrument. The plurality of response values includes contributions from variations between lots and variations between instruments. The core data analysis system "fits" the plurality of response values to a selected dose-response model using stochastic methods to estimate the probability distribution of each of the curve parameters that define the dose-response model. This probability distribution for each parameter acts as a prior probability distribution for fielded instruments. The system transmits the prior probability distribution for each curve parameter to fielded instruments so that each fielded instrument may determine the values of parameters appropriate to the individual instrument and reagent lot.

One or more of the probability distributions for model parameters may include contributions attributable to instrument-to-instrument variation or to variation between reagent lots. The method disclosed herein includes determination of these contributions for one or more of the parameters. A variety of methods may be suitable for such determination. For example, stochastic methods, in particular Markov Chain Monte Carlo methods, are of particular value in determining the contributions from each of these sources.

Core Curve Development Tool

FIG. 1 illustrates an example core curve development tool, according to an example embodiment of the present disclosure. The core curve development tool may be used to analyze data collected from various source instruments. While source instruments will typically include instruments operated by the manufacturer or supplier of instruments, they could also be any set of well-maintained instruments and properly adjusted instruments that could be used as a reference for constructing a standard model of instrument behavior. A core development tool may be provided using a computer system 10, including a conventional processor 12 and storage 14 accessible to the processor, including either conventional randomly accessible memory and/or mass storage. The computer system 10 may be in direct or indirect data communication with a plurality of analyzers 2 from which calibration test results may be received, e.g., via a network 4.

The computer system 10 can be located at an instrument supplier location, locally at a customer location, or a remote computer server not physically located at an instrument supplier location or at a customer location. For example, the remote computer server can be cloud computing, also known as on-demand computing. For example, if the computer system 10 is located at an instrument supplier location, or on a remote computer server, then the network 4 can be the Internet connected via Ethernet port, Wi-Fi, or cellular network. Alternatively, if the computer system 10 is located at a customer location, then the network 4 can be a local network, such as a centralized laboratory that has one or more analyzers 2 connected to the computer system 10. Further, a customer may have one or more laboratories located at different geographical locations, wherein each laboratory can have one or more analyzers 2. As such, the computer system 10 can be located at one customer location but because there may be a plurality of analyzers 2 located at different geographical locations, the one or more analyzers 2 can be connected to the computer system 10 via the Internet connected via Ethernet port, Wi-Fi, or cellular network. Alternatively, the customer may utilize a computer system 10 located on a remote computer server, where one or more analyzers 2 are located at a single customer location. Further, the customer may have a plurality of analyzers 2 located at different geographical locations, and the customer may utilize a computer system 10 located on a remote computer server.

Additionally, the calibration test results may be reported from one or more analyzers 2 over a network 4 to a computer system 10 using a remote diagnosis and instrument performance reporting tool. An example of a remote diagnosis and instrument performance reporting tool is the Beckman Coulter ProService Remote Service Application. The Beckman Coulter ProService Remote Service Application can provide a secure and continuous connection over the network 4 to one or more analyzers 2 using a Remote Application Processor ("RAP") box. The RAP box can connect one or more analyzers 2 to the computer system 10 by way of the Internet via Ethernet port, Wi-Fi, or cellular network. The analyzers 2 can send the instrument data, such as calibration test results, to the RAP box. The RAP box then secures this data and forwards it to the computer system 10. All communications between the analyzers 2 and the computer system 10 can be coordinated through the RAP box. The RAP box can connect to the network 2 using a static or Dynamic Host Configuration Protocol ("DHCP") IP address. The RAP box can include hardware having computer processing boards and connection ports capable of providing a secure transfer of instrument data, such as calibration test results, from one or more analyzers 2 to the computer system 10. For example, the RAP box can have one or more Ethernet connection ports, one or more computer processing boards for Wi-Fi or cellular network connectivity, an electrical outlet connection port, or any combination of the foregoing.

The RAP box can have an internal firewall to provide a secure and continuous transfer of instrument data, such as calibration test results, from one or more analyzers 2 to the computer system 10. This internal firewall can create a private instrument network which isolates the one or more analyzers 2 from other network traffic that exist on the network 2. Furthermore, the RAP box can secure the data transmission from the one or more analyzers to the computer system 10 by the following one or more mechanisms. First, the outbound-initiated data messages are secured via encryption and sent through a firewall via HTTPS on Port 443, the standard port for secure Internet usage. Data is transmitted during Secure Sockets Layer ("SSL"), which is a protocol for transmitting information securely via the Internet. SSL creates a secure connection between a client and a server, over which data can be sent securely. Dual certification authentication helps prevent unauthorized access to transmitted data, An example of a SSL connection is the 128 bit AES, FIPS compliant encryption algorithm. Another mechanism that the RAP box can secure the data is using a Remote Desktop Sharing ("RDS") session. An RDS session is held through a secure Virtual Private Network ("VPN") tunnel, which encapsulates the session between one or more analyzers 2 and the computer system 10 to ensure no third-party interception of the data being transmitted.

The computer system 10 may have access to the core calibration test results from an archive that has previously stored them. A software program 20 may be stored in the storage 14 and accessible for execution by the processor 12. The software program 20 may include multiple libraries, executables, or modules, which may be provided in any conventional computer language. The software program 20 may be configured to receive core calibration results, e.g., the data from calibrator samples in the core calibration procedure, and to analyze these results to produce core calibration information for use on individual analyzers. For example, the software program 20 may be used to create core calibration curve data based on the data from the core calibration procedure, and to generate the parameters for a core calibration curve. The software program 20 may run on any conventional computer processor, either onboard the instruments used in the core calibration, or more commonly, in data communication with those instruments.

The software program 20 may include model libraries 22. The model libraries 22 may include a pre-determined set of parametric equations that can be deployed for describing the core calibration curve. The pre-defined mathematical models may include, for example, a four parameter logistic nonlinear regression model ("4PL"), a five parameter logistical nonlinear regression model ("SPL"), and/or linear interpolation models.

The 4PL model equation, where x is concentration of the analyte and F(x) is the response value of the analyzer, is typically given by $$F(x)=(((A-D)/(1+((x/C)^B)))+D$$

Here D is the minimum response asymptote, which in a sandwich-type curve represents that the response value to a calibrator with zero concentration of analyte (or as the response value to a calibrator with an infinite concentration of analyte in a competitive assay). B is the hill slope or slope factor, which represents the maximal slope of the curve, which may be positive or negative. C is the inflection point, which is the point on the curve where the curvature changes sign, e.g., where the curve changes from being concave upwards to concave downwards. A is the maximum response asymptote, which in a sandwich-type curve that represents the response value for an infinite standard concentration. Typically, 4PL curve fits are symmetric around the inflection point and monotonic (either increasing or decreasing). In some cases, the 4PL model assumes that scatter of the measurement has a normal (or Gaussian) distribution, and that the standard deviation of the scatter is the same for all values of x. However, the Bayesian inference framework can also accommodate other distributions. For example, the standard deviation of the scatter in instrument response may be functionally related to analyte concentration and thus, may be non-constant. The precision profile (the relationship of the standard deviation of the scatter to analyte concentration) may be estimated using regression analysis of standard deviation of instrument response versus concentration of analyte before Bayesian estimation is applied to model parameters of interest.

The software program 20 may also include modules 24 for producing a probability distribution for model parameters such as the 4PL or SPL models discussed above. Each calibrator response signal is measured multiple times on multiple instruments using multiple assay lots. The probability distributions for each model parameter may include contributions related to the instrument, to the assay lot, to a combination of the instrument and the assay lot, or contributions that are independent of instrument and assay lot. In some embodiments, the software program 20 implements a stochastic process to form the probability densities based on the measured response signals to each of the calibrators. A suitable stochastic method is a Markov chain Monte Carlo algorithm. Markov chain Monte Carlo methods stochastically estimate a probability distribution based on a Markov chain, a memory-less simulation method that uses statistically correlated sampling of the distribution. Markov chain Monte Carlo methods are well known in the art and will not be further described.

The stochastic process used produces a distribution of possible parameter values. In some embodiments, the stochastic process may build a distribution based upon a linear combination of contributions related to the instrument, to the assay lot, to a combination of the instrument and the assay lot, or contributions that are independent of instrument and assay lot. In other embodiments, the stochastic process may build a distribution based upon a log-linear combination of contributions related to the instrument, to the assay lot, to a combination of the instrument and the assay lot, or contributions that are independent of instrument and assay lot. There may be interdependent contributions of assay lots and instruments, and these may also be included in producing the distributions.

The type of model used and the probability distributions for each parameter together constitute the core calibration information.

The software program 20 may also include visualization tools 26, which may provide a set of software based user interfaces on a display 30. The display may be provided on or in direct communication with the computer system 10, or on any device, such as another computer, tablet, the like that is accessible to a user and that is in data communication with the computer, e.g., through a network. The visualization tools 26 enable the outputs of the software program 20 (or modifications of the outputs including individual instrument-specific or lot-specific dose response curves calculated from a subset of the signals) to be inspected visually and quantified via a set of pre-determined or user-defined test statistics. The visualization tools also enable a developer to inspect and quantify the multiple options available for model choice.

Information Transmission

Fielded instruments are configured to receive the core calibration information. Individual instruments may be configured to receive results calculation information about a reagent when a reagent pack is loaded on the instrument. For example, a reagent pack may include an information storage device, such as a barcode, a 2-D graphical code, or an electronic memory (including contact memories and wireless memories such as RFID), whereby each reagent pack loaded on the instrument communicates results calculation information to the instrument. Included with this results calculation information is core curve information needed to translate signals (such as RLU signals) from the instrument into reportable patient results. The results calculation information may be readable from the reagent pack, or alternatively, may be retrievable remotely, e.g., from a server, based on reagent identification information provided with the reagent pack. For example, the core calibration information and/or the results calculation information can be sent from the computer system 10 to one or more analyzers 2 over the network 4 using the Beckman Coulter ProService Remote Service Application.

Instrument Processing

Fielded instruments may include software instructions that combine core calibration information with calibration adjuster signals to translate signals from the instrument, e.g. relative light unit ("RLU") signals into reportable patient results. Instrument software may be located onboard the instrument, or on a separate computer system in communication with the instrument. This software may also display to the end user the instrument-specific, lot specific dose-response curves well as any additional information needed by the end user to assess the performance and quality of their calibration processes.

Figure 2:
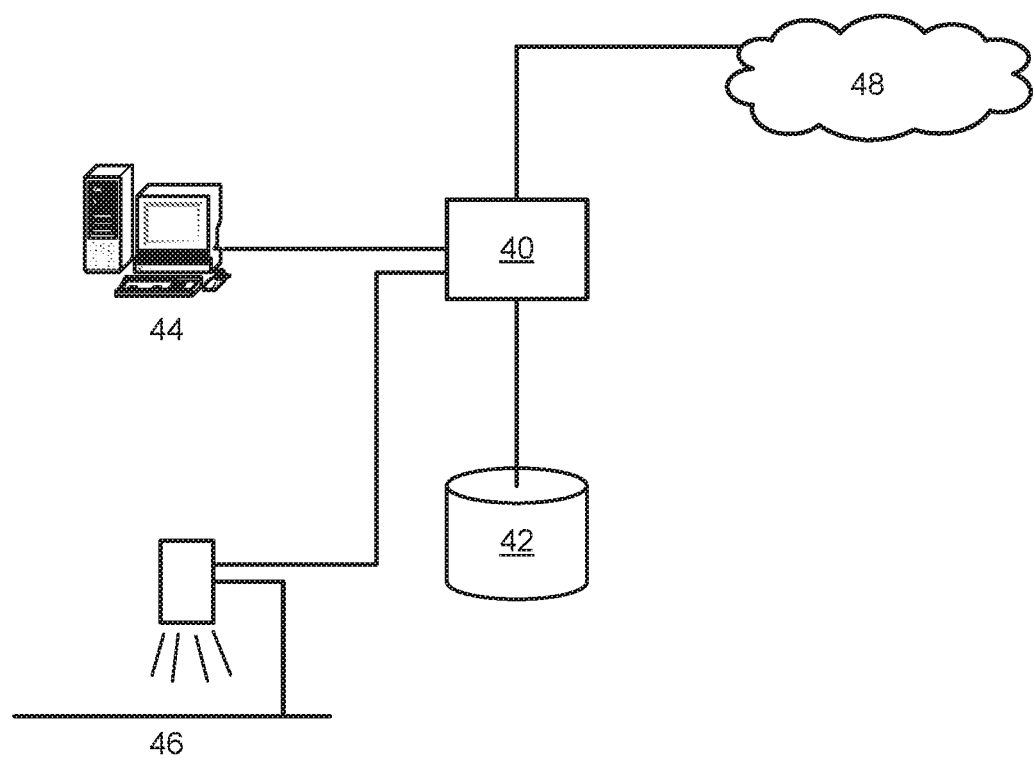
FIG. 2 illustrates an example analyzer, according to an example embodiment of the present disclosure.

FIG. 2 illustrates an example instrument, according to an example embodiment of the present disclosure. The instrument may be, e.g., an immunoassay analyzer, clinical chemistry analyzer, or nucleic acid analyzer of the same type as was used to construct core calibration information described above. The instrument may include a measurement device 46, for example an optical or electrical detection system configured to measure response signals of an analyte using a reagent from an assay lot. It will be appreciated that such a system will generally be configured to measure many different types of analytes with different types of reagents, under software control, and generally with end user input. The system is controlled by a computer processor 40, which may communicate with the end user through any conventional user input-output interface 44, either locally through some sort of display and input device(s), or remotely over a network 48.

The processor 40 operates under software control and is in communication with the measurement device 46. Storage 42 may be part of the processor 40 and or provided in communication with the processor, and may store software for control of the processor, information needed to process and analyze sample, and the results of such samples. Similar to the embodiment of FIG. 1, the processor 40 can be located at an instrument supplier location, locally at a customer location, or on a remote computer server not physically located at an instrument supplier location or at a customer location. The processor 40 may be configured to receive core calibration information (including the probability distributions for each model parameter) based on measurements of response values to a set of calibrators on a plurality of other instruments. For example, this may occur automatically when an end user loads a reagent of a particular type into the analyzer, as described above. Alternatively, the processor 40 can receive the core calibration information from the network 48 by way of the Beckman Coulter ProService Remote Service Application.

The core calibration information may be supplied with the reagent (e.g., in a machine readable form accompanying or part of the packaging), or the system may use information read from the packaging of the reagent or input by the end user to locate the information remotely, e.g., by communicating with a server that provides the information from the instrument supplier or source. The processor 40 may also be configured to receive, from the measurement system 46, information based on measurements of response values of one or more calibration adjusters on the instrument using the selected assay lot. The system may prompt an end user to perform these calibration adjustment runs from time to time, e.g., when a new reagent lot is loaded. The processor 40 combines the measured response signals from the one or more calibration adjusters with the core calibration information to produce an instrument-specific, assay-reagent-lot-specific, dose response model (a "local curve").

To produce a local curve, the processor 40 uses the probability distributions for each parameter from core calibration information as a prior probability distribution in a Bayesian inference procedure. Adjuster samples run on the selected instrument 46 using the selected lot provide information about the signal level for a given combination of reagent lot and instrument. The system uses Bayesian inference to combine the transmitted prior probability distribution for each model parameter and the adjuster data to produce a posterior probability distribution for each model parameter. The system then assigns to each model parameter a single value to construct the local curve. The value may correspond to a measure of central tendency of the posterior probability distribution for that parameter. The local curve thus produced uses the assigned data reduction model (such as a 4PL, 5PL, or other model) with parameter values determined from the combination of the core curve information and the local adjuster response signals. This reverses the typical paradigm of factory calibration, while achieving the same or better results. It can eliminate lot-specific factory curves, and the corresponding requirement to match adjusters and with each reagent lot.

Further, in embodiments where the core calibration information breaks out contributions attributable to between instrument variations, the characteristics of individual instruments can be adaptively estimated over time, and used to reject outlier data or indicate significant instrument shifts.

When an experimental run is made for a test sample, for example under instruction by the end user, the processor 40 may receive measurements of the unknown sample made on the instrument 46 using the selected assay lot, and, based on these measurements the processor 40 may determine the dose of the unknown sample from the measured response based on the local curve. The result is thus derived from the core calibration information, the information based on response signals of one or more calibration adjusters, and the response signals of the unknown sample. For example, the processor 40 may use a model, described elsewhere, to determine whether the proper thresholds for indicating an analyte has been detected at a particular dose and with a particular confidence, based on the core calibration procedure. Alternatively it may report measured data and how that data should be interpreted using dose response probability distributions based on the previously obtained calibration results, in any graphical representation chosen by the end user from amongst various options presented for display.

Calibration Adjusters

Calibration adjusters are a set of calibration materials that have a pre-determined concentration. These samples may be run on an instrument to determine the response of the individual analyzer using a selected assay lot. The calibration samples may be a subset of the calibrators used in core analysis, or, alternatively, they may be different calibrators which are particularly chosen for use as an adjuster. It will be appreciated that the adjuster may be tailored to the specific type of reagent, or to the particular reagent lot.

Example Procedures

Figure 3:
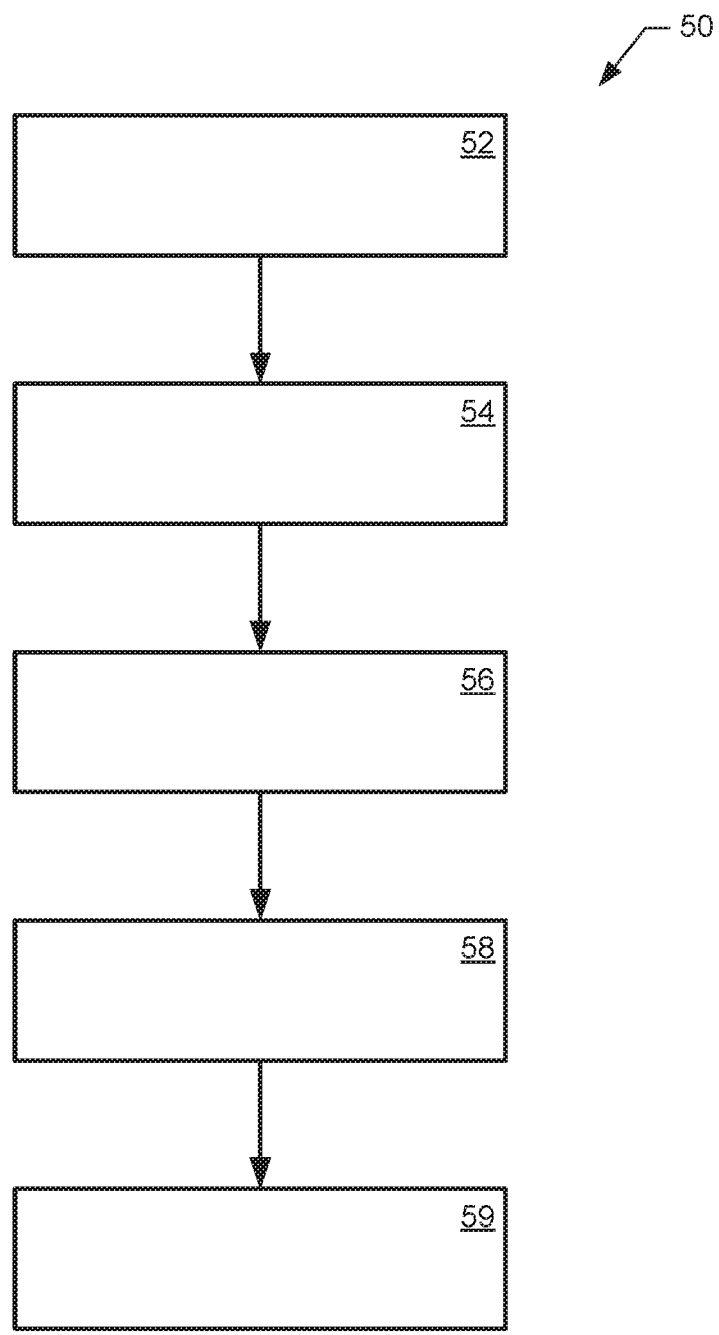
FIG. 3 illustrates an example procedure for determining a dose of an analyte in an unknown sample on an instrument, e.g., an immunoassay analyzer, clinical chemistry analyzer, or nucleic acid analyzer, according to an example embodiment of the present disclosure.

FIG. 3 illustrates an example procedure 50 for determining a dose of an analyte in an unknown sample on an instrument, e.g., an immunoassay analyzer, clinical chemistry analyzer, or nucleic acid analyzer, according to an example embodiment of the present disclosure. For purposes of illustration, the embodiment of FIG. 3 will be described with respect to an immunoassay analyzer. The immunoassay analyzer may include an onboard computer processor that performs the method, or alternatively the method may be performed at a separate computer processor that is in communication with and received data from the immunoassay analyzer.

In 52, core instrument dose-response information from a plurality of instruments of the same or similar type as the immunoassay analyzer may be received at the computer system. This information is based on the response signals of the plurality of source instruments to a set of calibrators having a known concentration of an analyte and using a plurality of assay lots. This information may be received in the form of parameter probability distributions for a model of a predetermined type. The model may be, for example a 4PL or 5PL model, which includes a plurality of parameters with prior probability values defined by the probability distributions. The probability distributions for each parameter are determined by stochastic "fitting" of the model to the response signals derived from the set of calibrators on the source instruments. Alternatively, a deterministic numerical integration process may be used. Each core dose-response model parameter is associated with at least one of a plurality of probability densities. Each probability density is a combination of a selected assay lot-specific density contribution and an instrument-specific density contribution.

In 54, information may be received for a particular assay lot. This information may be a model of a predetermined type such as a 4PL, a 5PL, or other parametric model, as well as limits of reportable ranges, reporting units, expiration dates, and other assay-specific information. It will be appreciated that both the core instrument dose response information and the particular assay lot information may be received together.

In 56, measurements of the particular instrument using calibration adjusters may be received at the computer processor. The measurements reflect the response of the particular instrument to calibration samples, e.g., run on the instrument by an end user prior to or during normal use for unknown samples. These results may then be used to calculate a posterior probability distribution for each parameter.

The computer processor also selects an individual value for each parameter, such as by determining a central value or typical value of each probability distribution and assigning this central value or typical value as the value for the parameter. The selected value may be the mean value of the distribution; other estimators such as the median or mode may also be used.

In 58, measurements of an unknown sample taken on the particular instrument using the selected reagent lot may be obtained and received at the computer processor.

In 59, the dose of analyte in the unknown sample may be determined using the parametric model with the individual values for each parameter, as determined at 56.

It will be appreciated that the above method can be performed, for example, using the computer system 10 illustrated in FIG. 1 using the software program also described in the discussion of FIG. 1, or on any other computer system or combination of computer systems that have access to measurements and information described above. As described above, the computer system, or the computer processor, can be located at an instrument supplier location, locally at a customer location, or on a remote computer server not physically located at an instrument supplier location or at a customer location.

Figure 4:
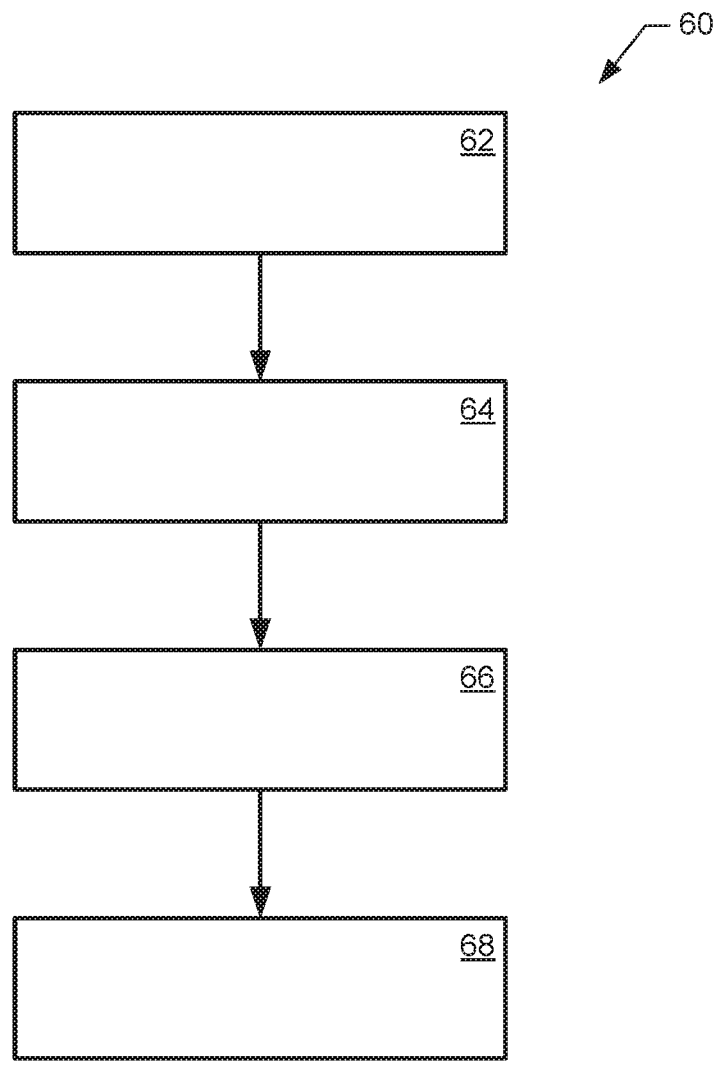
FIG. 4 illustrates an example procedure for generating a dose-response model for an instrument configured to determine an analyte with a selected assay lot, e.g., an immunoassay analyzer, clinical chemistry analyzer, or nucleic acid analyzer, according to an example embodiment of the present disclosure.

FIG. 4 illustrates an example procedure 60 for generating a dose-response model for an instrument configured to determine an analyte with a selected assay lot, according to an example embodiment of the present disclosure.

In 62, response values to a calibrator which are obtained using a plurality of source instruments and a plurality of source assay lots may be received, e.g., in a computer system in communication with the plurality of source instruments. The computer system, or the computer processor, can be located at an instrument supplier location, locally at a customer location, or on a remote computer server not physically located at an instrument supplier location or at a customer location. The calibrator presents a known concentration of an analyte to be measured on the source instrument. Multiple calibrators with different concentration may be used to measure a range of responses with different concentrations. Measurements of the identical calibrators may be taken on multiple instruments, with all or some of the instruments being used for all or a subset of the different calibrators. Generally these are different instruments than the instrument for which the dose-response model is intended to be used in testing unknown samples.

In 64, a selected model, e.g., a parametric model, such as the 4PL model described elsewhere, may be used to generate a core dose-response curve based on the measurements taken in 62. The core dose-response curve may include a parameter estimate of a model parameter, or of multiple parameters that fit the model to the response values of the calibrator. Each parameter estimate is associated with a probability density. The probability density may include a combination of a lot-specific density contribution and an instrument-specific density contribution.

In 66, a calibration adjuster, generally a smaller set of calibration samples of known analyte concentration, may be tested on a particular instrument with a selected assay lot. The calibration adjuster may be, but need not be, a subset of the calibrators used in the core testing. The particular instrument is typically not one of the instruments used in producing the core dose response-curve, but is typically of an identical type. For example, the adjuster may be used at the time cartridges containing a particular assay lot are loaded into the analyzer. Measurements of the calibration adjuster samples may be taken using the particular assay lot.

In 68, these measurements of response to the calibration adjuster samples, together may then be used to adjust the dose response curve for the particular instrument, for example by adjusting the core dose response curve for the particular reagent based on the results measured using the calibration adjuster.

It will be appreciated that the above method can be performed, for example, using the computer system 10 illustrated in FIG. 1 using the software program also described in the discussion of FIG. 1, or on any other computer system or combination of computer systems that have access to measurements and information described above. As described above, the computer system, or the computer processor, can be located at an instrument supplier location, locally at a customer location, or a remote computer server not physically located at an instrument supplier location or at a customer location.

Figure 5:
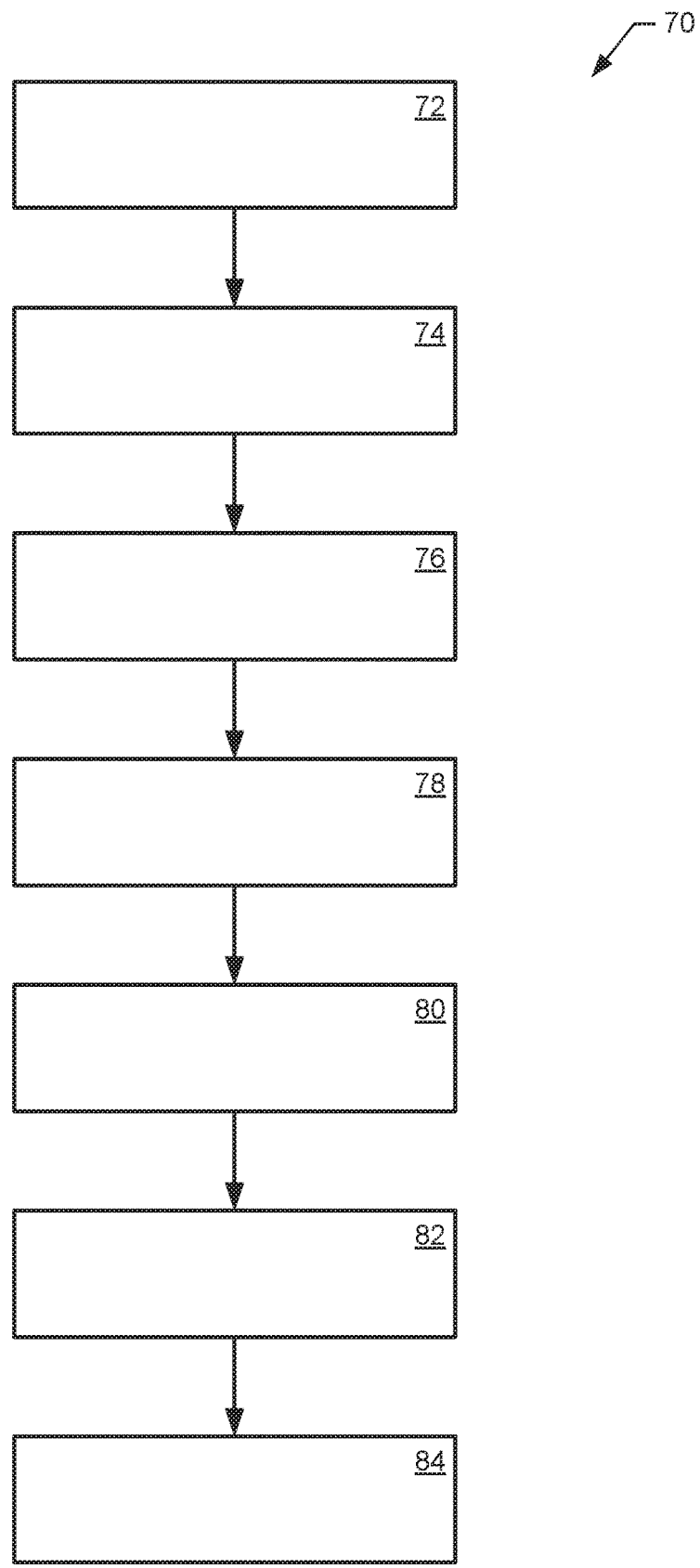
FIG. 5 illustrates an example procedure for determining a dose of an analyte in an unknown sample on an instrument using a selected assay lot, according to an example embodiment of the present disclosure

FIG. 5 illustrates another example procedure 70 for determining a dose of an analyte in an unknown sample on an instrument using a selected assay lot, according to an example embodiment of the present disclosure.

In 72, the response values to a set of calibrators may be measured using a plurality of source instruments. This may be performed similarly to the same operation described in the other example procedures above. Measurements are taken using the selected assay lot, and optionally measurements using different assay lots may also be included in some scenarios.

In 74, a core dose-response curve may be defined. The core dose response curve may correspond to a pre-selected model, e.g., a parametric model based on several parameter estimates, as a 4PL or 5PL model. The parameter estimates may be made to fit the model the response values of the source instruments to the set of calibrators that were measured in 72. Each core dose-response curve model parameter estimate may be associated with a corresponding probability density. Each probability density may be a combination of a reagent assay lot specific density contribution for the selected assay lot and an instrument specific density contribution.

In 76, the parameter estimates and probability densities may be transmitted to an instrument which will be used to evaluate unknown samples. If multiple models are used, the identity of the appropriate model may also be transmitted.

In 78, the response values of one or more of the instrument to one or more calibration adjusters may be obtained, using the selected assay lot.

In 80, based on the response values in 78, an instrument-specific, selected lot specific model, e.g., a dose response curve using a parametric model, may be generated for the instrument. This model may be also based on the transmitted parameter estimates and probability densities.

In 82, the instrument may be used to obtain response values for an unknown sample using the selected assay lot.

In 84, the dose of the analyte in the unknown sample may be determined from the measured response in 82, using the instrument-specific, selected lot-specific dose-response curve obtained in 80.

It will be appreciated that the above method can be performed, for example, using the computer system 10 illustrated in FIG. 1 using the software program also described in the discussion of FIG. 1, or on any other computer system or combination of computer systems that have access to measurements and information described above. As described above, the computer system, or the computer processor, can be located at an instrument supplier location, locally at a customer location, or on a remote computer server not physically located at an instrument supplier location or at a customer location.

Figure 6:
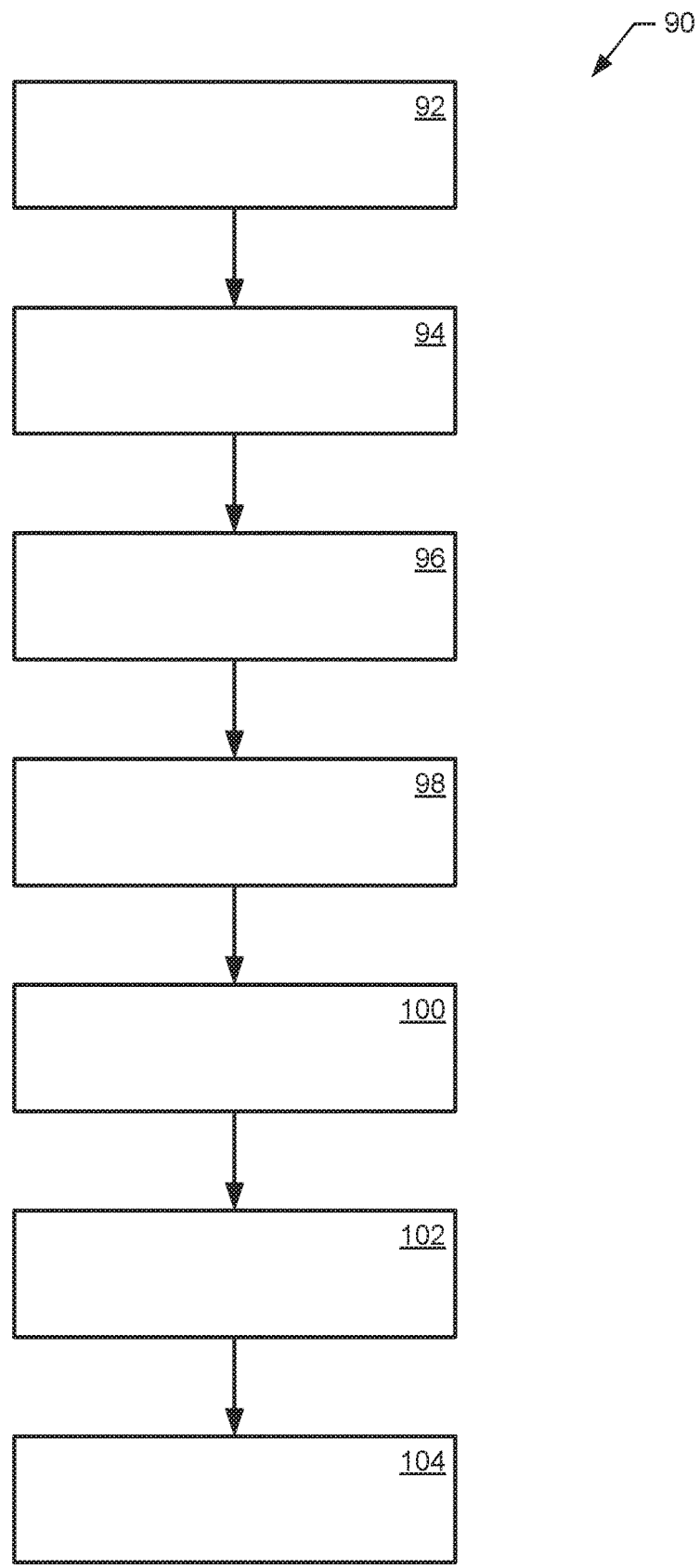
FIG. 6 illustrates an alternative example procedure for determining a dose of an analyte in an unknown sample on an instrument using a selected assay lot, according to an example embodiment of the present disclosure.

FIG. 6 illustrates an alternative example procedure 90 for determining a dose of an analyte in an unknown sample on an instrument using a selected assay lot, according to an example embodiment of the present disclosure. The elements of the procedure are similar to the elements of the procedure illustrated in FIG. 5, except as noted below.

In 92, the response values to a set of calibrators may be measured using a plurality of source instruments. Measurements are also taken using a plurality of assay lots.

In 94, a core dose-response curve may be defined, as in 74. The procedure may be adapted to take advantage of the fact that multiple assay lots are analyzed.

In 96 an address or pointer identifying a stored representation of parametric adjustments may be determined. The address may identify a location on the analyzer where the representation is stored, e.g., in memory, or alternatively a remote location from where the information may be retrieved, e.g., by downloading over the Internet. This address indirectly addresses parametric adjustments that correspond to the plurality of parameter estimates and probability densities obtained in 96. The parameter estimates and address or pointer may be transmitted to instrument which will be used to evaluate unknown samples.

In 98, the response values of one or more of the instrument to one or more calibration adjusters may be obtained, using the selected assay lot.

In 100, an instrument-specific, selected lot specific model, e.g., a dose response curve using a parametric model, may be generated for the instrument. This model may be also based on the transmitted parameter estimates, replicates of the stored representations of parametric adjustments that are accessed using the address or pointer, and the response values obtained using the calibration adjusters on the selected instrument using the particular selected assay lot.

In 102, the instrument may be used to obtain response values for an unknown sample using the selected assay lot.

In 104, the dose of the analyte in the unknown sample may be determined from the measured response in 102, using the instrument-specific, selected lot-specific dose-response curve obtained in 100.

In the above example procedures, such as the ones illustrated in FIGS. 3, 5, and 6, it should be appreciated that there are two variant approaches to conducting the initial test runs. The variation across source instruments can be determined separately, without reference to the particular assay lot. Then the variation due to the assay lot may be determined in a separate set of tests, and the contribution of both can be combined to produce a combined response curve. Alternatively, variation across the source instruments for the particular reagent lot can be tested, and the core response curve produced directly from those measurements, possibly without consideration of the responses using other reagent lots. In one implementation, the probability density of the model parameters may include a correlated lot x instrument contribution, for the particular reagent lot.

In the above example procedures like the ones illustrated in FIGS. 3, 5, and 6, the model may be a four-parameter logistic model. It will be appreciated that other appropriate models, for example a five parameter logistic model may be alternatively used. The four-parameter logistic model may take the form of:

$$f(x) = \frac{a_{ij} - d_{ij}}{1 + \exp\{b_{ij}(\ln(x) - \ln(c_{ij}))\}} + d_{ij}$$

In this equation, x denotes dose, f(x) denotes response value associated with dose x. In addition, a, b, c, and d denote the model parameters. Further index i denotes the instruments and index j denotes reagent lots. Here, the parameters may have the following interpretation $$\ln(a_{ij} - d_{ij}) = \alpha_0 + \alpha_{Lot_j} + \alpha_{Instrument_j} + \alpha_{Lot \times Instrument_{ij}}$$

$$b_{ij} = \beta_0 + \beta_{Lot_j} + \beta_{Instrument_j} + \beta_{Lot \times Instrument_{ij}}$$

$$\ln(c_{ij}) = \gamma_0 + \gamma_{Lot_j} + \gamma_{Instrument_j} + \gamma_{Lot \times Instrument_{ij}}$$

$$\ln(d_{ij}) = \xi_0 + \xi_{Lot_j} + \xi_{Instrument_j} + \xi_{Lot \times Instrument_{ij}}$$

Here, $\alpha$, $\beta$, $\gamma$, and $\xi$ each denote contributions to the respective parameters a, b, c, and d. The probability density in the model described above may include contributions from one or more of the model parameters, and may include contributions from both lot specific density and instrument specific density, which may be summed or combined in other ways. This contribution may be estimated as the log of lot specific contribution and instrument-specific contribution.

Using the above model, the core dose response curve may be calculated by determining a prior probability distribution using a stochastic method, such as a Markov Chain Monte Carlo or other Monte Carlo method. Alternatively, deterministic methods such as numerical integration or Gaussian quadrature integration may be used.

It will be appreciated that the above method can be performed, for example, using the computer system 10 illustrated in FIG. 1 using the software program also described in the discussion of FIG. 1, or on any other computer system or combination of computer systems that have access to measurements and information described above. As described above, the computer system, or the computer processor, can be located at an instrument supplier location, locally at a customer location, or on a remote compute server not physically located at an instrument supplier location or at a customer location.

Remote Reporting

The raw calibration data collected, and/or the calibration results determined using the example procedures described in this specification for instruments such as the one described in the previous section may be reported from the instrument over a network to a central diagnosis and service center, e.g., using the Beckman-Coulter ProService Application, or other remote diagnosis and instrument performance reporting tools. If the raw calibration data is reported in this manner, the analysis of the calibration data may be done remotely from the instrument. Alternatively, this may still be done locally on the instrument, and with the analysis being sent either together with, or without the raw calibration data. Whether the analysis is done locally or remotely, the calibration data and results may then be used as part of remote diagnosis and service procedures, for example, to identify if problems with a particular instrument might be the result of improper calibration, or to conduct ongoing quality control analysis such as identifying drift or other indications that a machine requires a particular type of servicing. The data calibration data may also be used in conjunction with other sorts of information from an instrument sent to central diagnosis as part of an overall diagnosis, troubleshooting, or quality control model, such other information including instrument status and events, instrument subsystem vital signs, such as temperature, pressure, and voltages, subsystem/module specific parameters, including analytical system components, motion controls, and fluidic systems, actual analytic results (generally with patient identifiable data masked), system identifiers and statistics, software version information, instrument configurations, and metering data.

Example I

Figure 7:
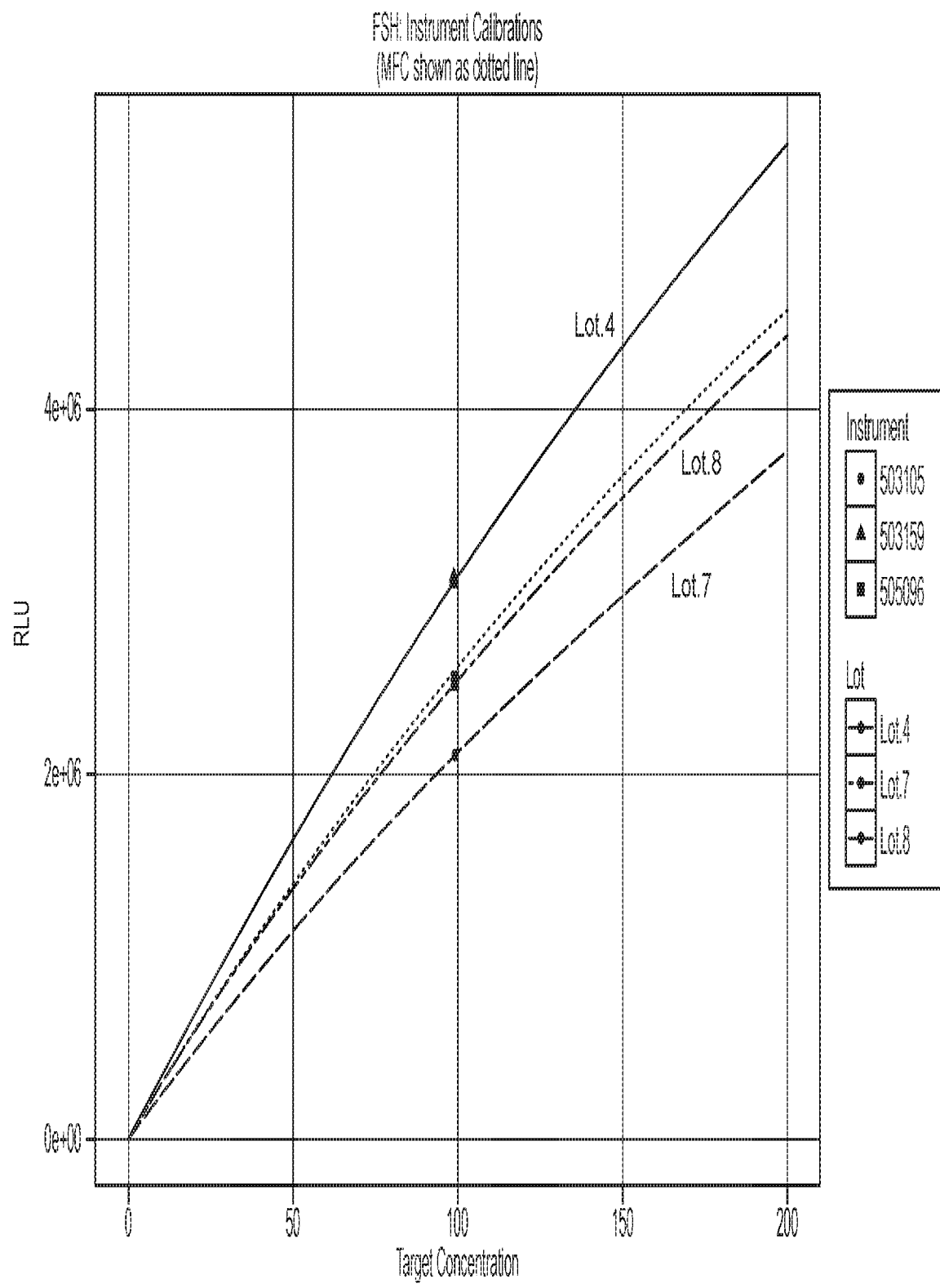
FIG. 7 illustrates calibration results for a first example reagent obtained using a conventional two-point adjuster calibration procedure.

FIG. 7 illustrates calibration results obtained using a conventional two point adjuster for calibration. The data represents detection data for follicle stimulation hormone ("FSH") calibration samples measured on immunoassay analyzers. The Y axis represents relative light units ("RLU"), which are unitless photon counts from a luminometer of an immunoassay analyzer. The X axis represents the target concentration of the calibration samples of FSH. Each of three instruments was tested for calibration using a particular reagent lot, lot 4 for instrument 503159, lot 7 for instrument 503105, and lot 8 for instrument 505096. Two tests were run for each instrument lot pair, at two different concentrations (0 and 100). (It is difficult to discriminate between the pairs of tests because they are quite close on the plot). The resulting calibration curves for the three instruments are show as solid lines. The dotted line represents a master core calibration curve ("MCC") obtained using the process of the present disclosure, as discussed further in FIG. 8. The MCC can be an example of a core dose-response curve, an instrument-specific, lot-specific dose-response curve, or an adjusted dose-response curve using the models described in the present disclosure. As shown in FIG. 7, the MCC should provide a better calibration than the top solid curve or the bottom solid curve.

Figure 8:
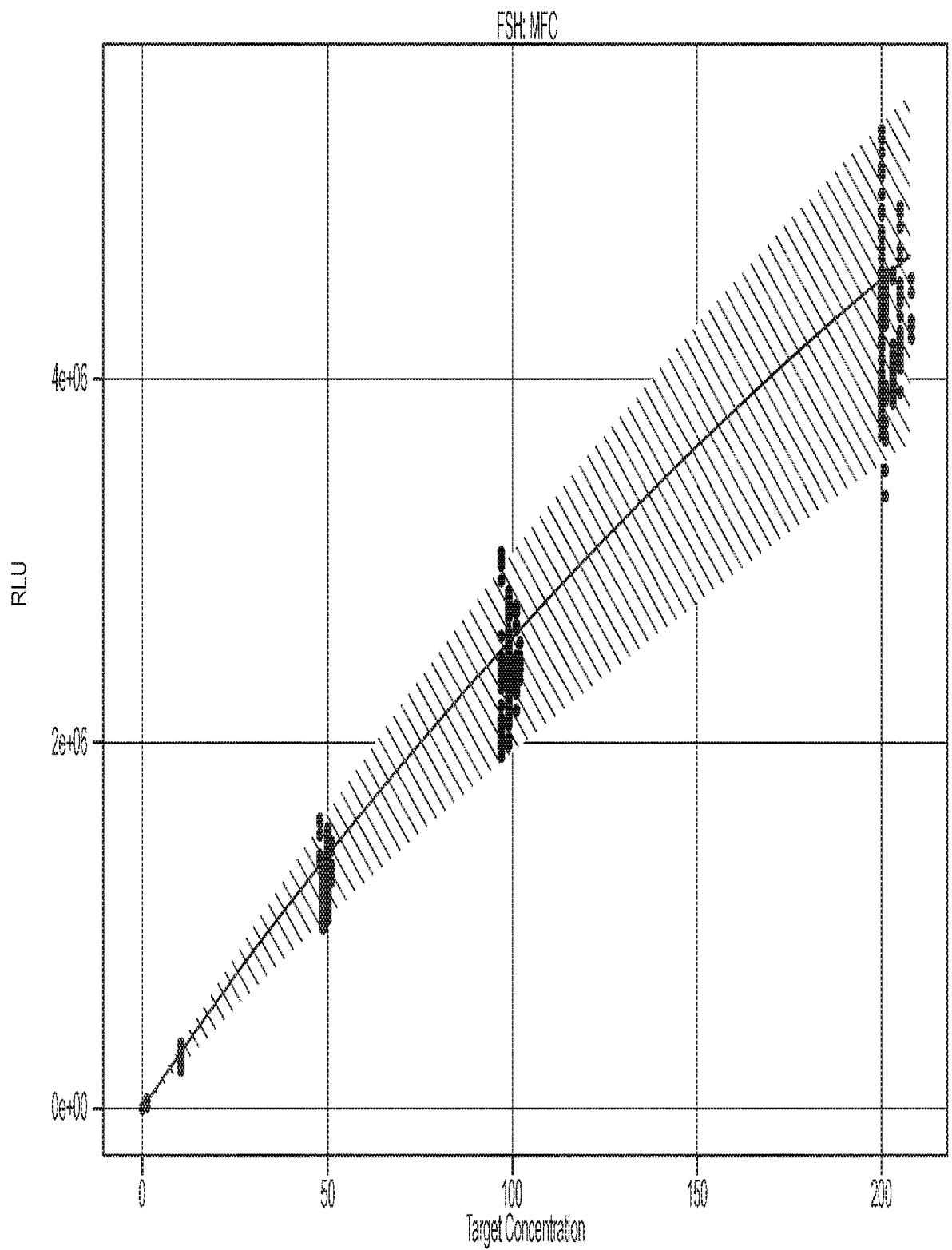
FIG. 8 illustrates calibration results for a first example reagent, obtained using an example embodiment of the present disclosure.

FIG. 8 illustrates calibration results obtained using the process of the present disclosure. The axes are the same as in FIG. 7. The solid line represents the MCC obtained using the process of the present disclosure. The MCC can be an example of a core dose-response curve, an instrument-specific, lot-specific dose-response curve, or an adjusted dose-response curve using the models described in the present disclosure. The gray shaded region shows the observed instrument variability. The width and horizontal variation of the points within the groups of samples reflects deviation between calibrator lots. Multiple calibration results are plotted from multiple lots on multiple machines. The instrument-specific curve can be used to better interpret the calibration data.

Example II

Figure 9:
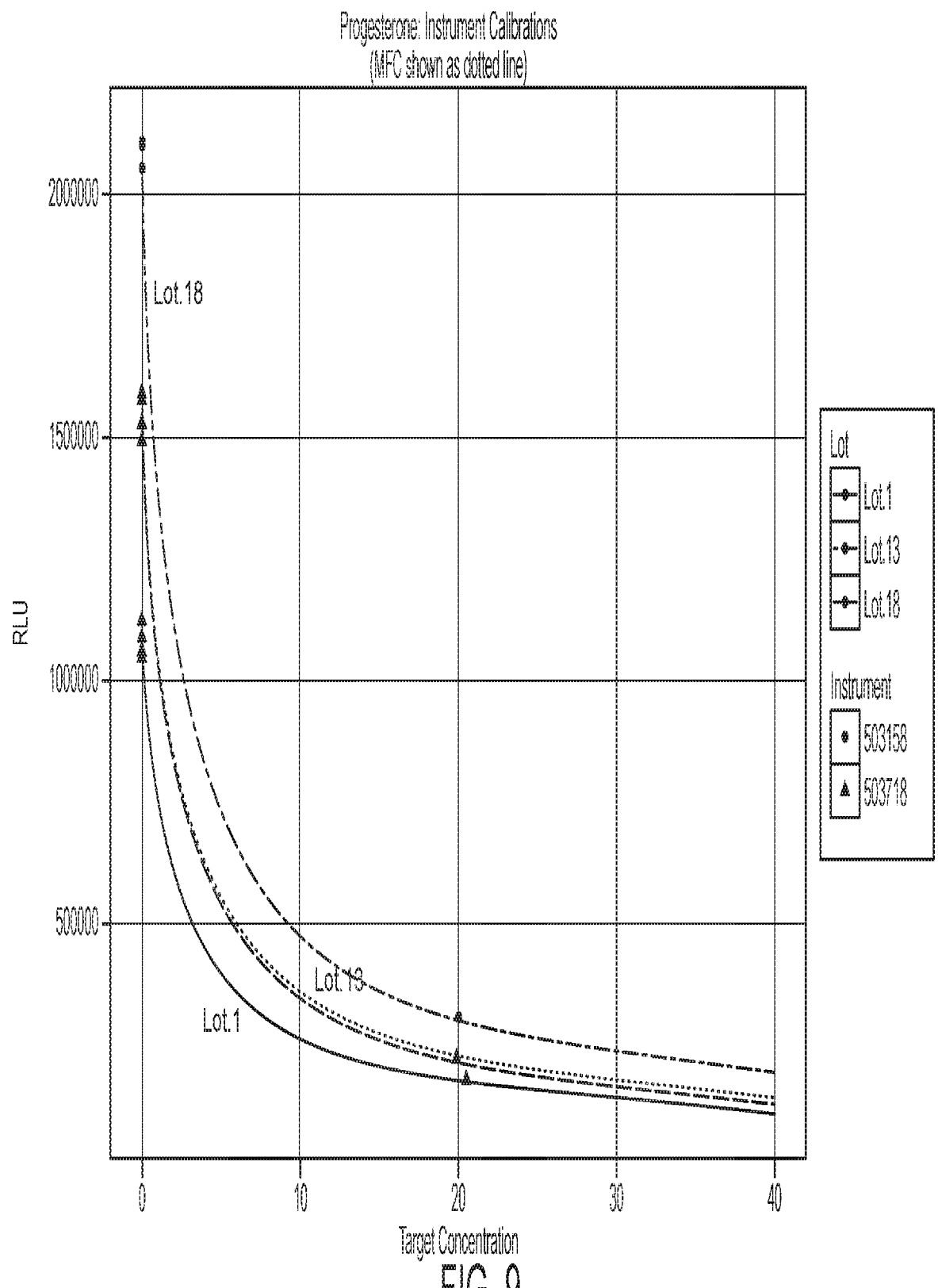
FIG. 9 illustrates calibration results for a second example reagent, obtained using a conventional two-point adjuster calibration procedure.

FIG. 9 illustrates calibration results obtained using conventional two point adjuster methods similar to FIG. 7. However, in this case the reagents being tested are calibrator samples of Progesterone, which has a decreasing response with concentration, as opposed to the increasing response of FSH. The dotted line represents the master core calibration curve ("MCC") obtained using the process of the present disclosure, as discussed further in FIG. 10. The MCC can be an example of a core dose-response curve, an instrument-specific, lot-specific dose-response curve, or an adjusted dose-response curve using the models described in the present disclosure. The top solid curve indicates a two point adjuster calibration curve for reagent lot 1 on machine 503158. The middle solid curve represents a two point adjuster calibration curve for reagent lot 13 on instrument 503718. The two point adjuster method does not take advantage of the prior knowledge of the machine calibration data for the particular machine; accordingly the results from the calibration with one lot do not assist in the calibration of the machine with the second lot. The bottom solid curve represents a two point adjuster calibration curve for reagent lot 18 on the same instrument. As shown in FIG. 9, the MCC should provide a better calibration than the top solid curve or the bottom solid curve.

Figure 10:
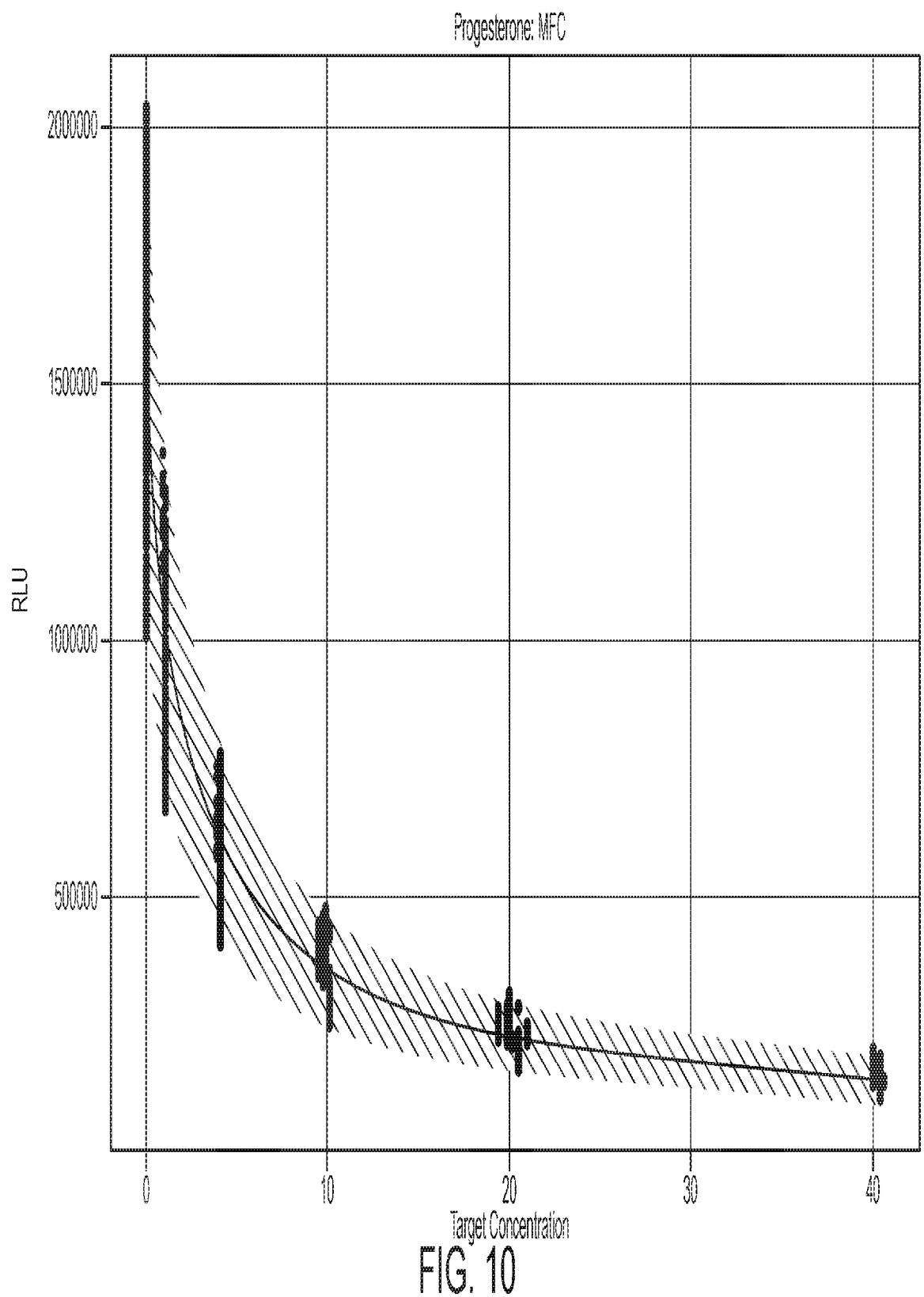
FIG. 10 illustrates calibration results for a second example reagent obtained using an example embodiment of the present disclosure.

FIG. 10 illustrates calibration results in for Progesterone with the disclosed process being applied. The solid line represents the MCC obtained using the process of the present disclosure. The MCC can be an example of a core dose-response curve, an instrument-specific, lot-specific dose-response curve, or an adjusted dose-response curve using the models described in the present disclosure. It should be noted that particularly, for zero or low concentrations, the variability across machines and reagent lots is quite high. In contrast, for high concentrations, calibration sample inter-lot variability, which is reflected by the horizontal spread of the cluster of data points, is a much larger source of variability.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety to the extent each is consistent with the disclosure of this application.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

While the invention has been described with particular reference to preferred embodiments, it will be understood that variations can be made without departing from the spirit of the invention, and such variations are intended to fall within the scope of the appended claims. While the reagent is typically in the form of a liquid that is miscible with a sample, the reagent may be in a dry form.

It will be appreciated that all of the disclosed methods and procedures described above can be implemented using one or more computer programs or components. These components may be provided as a series of computer instructions on any conventional tangible computer-readable medium, including RAM, ROM, flash memory, magnetic or optical disks, optical memory, or other storage media. The instructions may be configured to be executed by a processor, which when executing the series of computer instructions performs or facilitates the performance of all or part of the disclosed methods and procedures.

The invention is claimed as follows:

1. A system for determining a dose of an analyte in an unknown sample using a reagent from a selected assay lot, the system comprising:
 a measurement device to measure response information of the analyte using a reagent from the assay lot; and
 a processor in communication with the measurement device, the processor configured to:
  receive a core dose-response curve defined by a model including at least one parameter estimate, wherein each parameter estimate is associated with at least one probability density, and wherein each probability density is a combination of a lot-specific density contribution and an instrument-specific density contribution;
  receive information based on measurements of response values of one or more calibrator adjusters on the instrument using the assay lot;
  receive a measured response of the unknown sample made on the instrument using the assay lot; and
  determine the dose of the analyte in the unknown sample using an instrument-specific, selected lot-specific dose-response curve and the measured response of the unknown sample, wherein the instrument-specific, selected lot-specific dose-response curve is generated using the model, the transmitted plurality of parameter estimates, the transmitted plurality of probability densities, and the response values of the one or more calibration adjusters.

2. The system of claim 1, wherein the model is a four-parameter logistic model and the at least one probability density includes a sum of a lot-specific density contribution and an instrument-specific density contribution.

3. The system of claim 2, wherein the four-parameter logistic model has form $$f(x) = \frac{a_{ij} - d_{ij}}{1 + \exp\{b_{ij}(\ln(x) - \ln(c_{ij}))\}} + d_{ij}$$

wherein x denotes dose, f(x) denotes response value associated with dose x, wherein a, b, c, and d denote the model parameters, and
wherein index i denotes instruments and index j denotes reagent lots.

4. The system of claim 3, wherein $\ln(a_{ij} - d_{ij}) = \alpha_0 + \alpha_{Lot_i} + \alpha_{Instrument_j} + \alpha_{Lot \times Instrument_{ij}}$ $b_{ij} = \beta_0 + \beta_{Lot_i} + \beta_{Instrument_j} + \beta_{Lot \times Instrument_{ij}}$ $\ln(c_{ij}) = \gamma_0 + \gamma_{Lot_i} + \gamma_{Instrument_j} + \gamma_{Lot \times Instrument_{ij}}$ $\ln(d_{ij}) = \xi_0 + \xi_{Lot_i} + \xi_{Instrument_j} + \xi_{Lot \times Instrument_{ij}}$ wherein α, β, γ, and ξ each denote contributions to the respective parameters a, b, c, and d and the respective subscripts denote the source of the contributions.

5. The system of claim 1, wherein the instrument-specific, lot-specific dose-response curve is generated using a process that includes applying Bayesian inference using a parameter from the at least one parameter estimate as a prior distribution and the measured response values of the one or more calibration adjusters to form a posterior distribution, and assigning a central measure of the posterior distribution as the value of the model parameter corresponding to the parameter estimate.

6. The system of claim 1, wherein the processor is further configured to generate the instrument-specific, selected lot-specific dose-response curve based on the model, the at least one parameter estimate, the at least one probability density, and the response values of the one or more calibration adjusters.

7. The system of claim 1, wherein the system is a system for determining the dose of the analyte in the unknown sample by ligand-binding analysis using the reagent from the selected assay lot.

8. A method for determining a dose of an analyte in an unknown sample on an instrument using a reagent from a selected assay lot, comprising:
    receiving, at a computer processor, a core dose-response curve defined by a model including at least one parameter estimate, wherein each parameter estimate is associated with at least one probability density, and wherein each probability density is a combination of a lot-specific density contribution and an instrument-specific density contribution;
    receiving, at the computer processor, information on measurements of response values of one or more calibration adjusters on the instrument using the selected assay lot;
    receiving, at a computer processor, an instrument-specific, selected lot-specific dose-response curve using the model, the transmitted plurality of parameter estimates, the transmitted plurality of probability densities, and the response values of the one or more calibration adjusters;
    receiving, at the computer processor, measurements of the unknown sample made on the instrument using the selected assay lot; and
    determining, at the computer processor, the dose of the analyte in the unknown sample using the instrument-specific, selected lot-specific dose-response curve and the measurements of the unknown sample.

9. The method of claim 8, further comprising the steps of:
    receiving, from a plurality of instruments, measured response values of one or more calibration adjustors on the plurality of instruments using one or more assay lots;
    generating an adjusted dose-response curve using the model, the at least one parameter estimate, the at least one probability density, and the measured response values of one or more calibration adjustors on the plurality of instruments using the one or more assay lots; and
    transmitting the adjusted dose-response curve to at least one instrument from the plurality of instruments.

10. The method of claim 9, wherein the model is a four-parameter logistic model and the at least one probability density includes a sum of a lot-specific density contribution and an instrument-specific density contribution.

11. The method of claim 10, wherein the four-parameter logistic model has form $$f(x) = \frac{a_{ij} - d_{ij}}{1 + \exp\{b_{ij}(\ln(x) - \ln(c_{ij}))\}} + d_{ij}$$

wherein x denotes dose, f(x) denotes response value associated with dose x, wherein a, b, c, and d denote the model parameters, and
wherein index i denotes instruments and index j denotes reagent lots.

12. The method of claim 11, wherein $$\ln(a_{ij} - d_{ij}) = \alpha_0 + \alpha_{Lot_i} + \alpha_{Instrument_j} + \alpha_{Lot \times Instrument_{ij}}$$

$$b_{ij} = \beta_0 + \beta_{Lot_i} + \beta_{Instrument_j} + \beta_{Lot \times Instrument_{ij}}$$

$$\ln(c_{ij}) = \gamma_0 + \gamma_{Lot_i} + \gamma_{Instrument_j} + \gamma_{Lot \times Instrument_{ij}}$$

$$\ln(d_{ij}) = \xi_0 + \xi_{Lot_i} + \xi_{Instrument_j} + \xi_{Lot \times Instrument_{ij}}$$

wherein $\alpha$, $\beta$, $\gamma$, and $\xi$ each denote contributions to the respective parameters a, b, c, and d and the respective subscripts denote the source of the contributions.

13. The method of claim 9, wherein the at least one probability density further includes a correlated lot x instrument contribution.

14. The method of claim 9, further including a plurality of model parameters and a plurality of probability densities, wherein each model parameter is associated with a probability density,
    wherein the plurality of model parameters includes parameters a, b, c, and d, and
    wherein the probability density associated with each of model parameters a, c, and d includes a logarithm of a sum of a respective lot-specific density contribution and a respective instrument-specific density contribution.

15. The method of claim 14, wherein the probability density associated with model parameter b includes a sum of a parameter b lot-specific density contribution and a parameter b instrument-specific density contribution.

16. The method of claim 9, wherein the model is a four-parameter logistic model and the at least one probability density includes a logarithm of a sum of a lot-specific density contribution and an instrument-specific density contribution.

17. The method of claim 8 wherein the model is a four-parameter logistic model and the at least one probability density includes a sum of a lot-specific density contribution and an instrument-specific density contribution.

18. The method of claim 17, wherein the four-parameter logistic model has form $$f(x) = \frac{a_{ij} - d_{ij}}{1 + \exp\{b_{ij}(\ln(x) - \ln(c_{ij}))\}} + d_{ij}$$

wherein x denotes dose, f(x) denotes response value associated with dose x, wherein a, b, c, and d denote the model parameters, and
wherein index i denotes instruments and index j denotes reagent lots.

19. The method of claim 18, wherein $$\ln(a_{ij} - d_{ij}) = \alpha_0 + \alpha_{Lot_i} + \alpha_{Instrument_j} + \alpha_{Lot \times Instrument_{ij}}$$

$$b_{ij} = \beta_0 + \beta_{Lot_i} + \beta_{Instrument_j} + \beta_{Lot \times Instrument_{ij}}$$

$$\ln(c_{ij}) = \gamma_0 + \gamma_{Lot_i} + \gamma_{Instrument_j} + \gamma_{Lot \times Instrument_{ij}}$$

$$\ln(d_{ij}) = \xi_0 + \xi_{Lot_i} + \xi_{Instrument_j} + \xi_{Lot \times Instrument_{ij}}$$

wherein $\alpha$, $\beta$, $\gamma$, and $\xi$ each denote contributions to the respective parameters a, b, c, and d and the respective subscripts denote the source of the contributions.

20. The method of claim 8, wherein the at least one probability density further includes a correlated lot x instrument contribution.

21. The method of claim 8, further including a plurality of model parameters and a plurality of probability densities,
    wherein each model parameter is associated with a probability density, wherein the plurality of model parameters includes parameters a, b, c, and d, and
wherein the probability density associated with each of model parameters a, c, and d includes a logarithm of a sum of a respective lot-specific density contribution and a respective instrument-specific density contribution.

22. The method of claim 21, wherein the probability density associated with model parameter b includes a sum of a parameter b lot-specific density contribution and a parameter b instrument-specific density contribution.

23. The method of claim 8, wherein the method is a method for determining the dose of the analyte in the unknown sample by ligand-binding analysis on the instrument using the reagent from the selected assay lot.

24. The method of claim 8, wherein the model is a four-parameter logistic model and the at least one probability density includes a logarithm of a sum of a lot-specific density contribution and an instrument-specific density contribution.

25. A method of generating a dose-response curve for an instrument configured to determine an analyte with a selected assay lot, the method comprising:
measuring response values to one or more calibrators using a plurality of source instruments and a plurality of assay lots;
generating a core dose-response curve defined by a model including a model parameter, wherein the core dose-response curve includes at least one parameter estimate of the model parameter that fits the model to the response values of the one or more calibrators, wherein the parameter estimate is associated with at least one probability density, and wherein the probability density is a combination of a lot-specific density contribution and an instrument-specific density contribution;
receiving, from the instrument, measured response values of one or more calibration adjusters on the instrument using the selected assay lot;
generating an instrument-specific, lot-specific dose-response curve using the model, the at least one parameter estimate, the at least one probability density, and the measured response values of the one or more calibration adjusters; and
transmitting the instrument-specific, lot-specific dose-response curve to the instrument.

26. The method of claim 25, wherein the step of generating the instrument-specific, lot-specific dose-response curve includes applying Bayesian inference using the probability estimate as a prior distribution and the measured response values of the one or more calibration adjusters to form a posterior distribution, and assigning a central measure of the posterior distribution as the value of the model parameter.

27. The method of claim 26, wherein the central measure is one of a median, a mode, or a mean.

28. The method of claim 26, wherein the model is a four-parameter logistic model and the at least one probability density includes a sum of a lot-specific density contribution and an instrument-specific density contribution.

29. The method of claim 28, wherein the four-parameter logistic model has form $$f(x) = \frac{a_{ij} - d_{ij}}{1 + \exp\{b_{ij}(\ln(x) - \ln(c_{ij}))\}} + d_{ij}$$

wherein x denotes dose, f(x) denotes response value associated with dose x, wherein a, b, c, and d denote the model parameters, and
wherein index i denotes instruments and index j denotes reagent lots.

30. The method of claim 29, wherein $$\ln(a_{ij} - d_{ij}) = \alpha_0 + \alpha_{Lot_i} + \alpha_{Instrument_j} + \alpha_{Lot \times Instrument_{ij}}$$

$$b_{ij} = \beta_0 + \beta_{Lot_i} + \beta_{Instrument_j} + \beta_{Lot \times Instrument_{ij}}$$

$$\ln(c_{ij}) = \gamma_0 + \gamma_{Lot_i} + \gamma_{Instrument_j} + \gamma_{Lot \times Instrument_{ij}}$$

$$\ln(d_{ij}) = \xi_0 + \xi_{Lot_i} + \xi_{Instrument_j} + \xi_{Lot \times Instrument_{ij}}$$

wherein α, β, γ, and ξ each denote contributions to the respective parameters a, b, c, and d and the respective subscripts denote the source of the contributions.

31. The method of claim 26, wherein the model is a four-parameter logistic model and the at least one probability density includes a logarithm of a sum of a lot-specific density contribution and an instrument-specific density contribution.

32. The method of claim 25, wherein the step of generating a core dose-response curve includes calculating a prior distribution using a stochastic method.

33. The method of claim 32, wherein the stochastic method includes a Markov Chain Monte Carlo method.

34. The method of claim 25, wherein the step of generating the instrument-specific, lot-specific dose-response curve includes a deterministic method that includes a numerical integration method.

35. The method of claim 25, wherein the method is a method of generating the dose-response curve for the instrument configured to determine the analyte by ligand-binding analysis with the selected assay lot.

36. The method of claim 25, wherein the model is a four-parameter logistic model and the at least one probability density includes a sum of a lot-specific density contribution and an instrument-specific density contribution.

37. The method of claim 36, wherein the four-parameter logistic model has form $$f(x) = \frac{a_{ij} - d_{ij}}{1 + \exp\{b_{ij}(\ln(x) - \ln(c_{ij}))\}} + d_{ij}$$

wherein x denotes dose, f(x) denotes response value associated with dose x, wherein a, b, c, and d denote the model parameters, and
wherein index i denotes instruments and index j denotes reagent lots.

38. The method of claim 37, wherein $$\ln(a_{ij} - d_{ij}) = \alpha_0 + \alpha_{Lot_i} + \alpha_{Instrument_j} + \alpha_{Lot \times Instrument_{ij}}$$

$$b_{ij} = \beta_0 + \beta_{Lot_i} + \beta_{Instrument_j} + \beta_{Lot \times Instrument_{ij}}$$

$$\ln(c_{ij}) = \gamma_0 + \gamma_{Lot_i} + \gamma_{Instrument_j} + \gamma_{Lot \times Instrument_{ij}}$$

$$\ln(d_{ij}) = \xi_0 + \xi_{Lot_i} + \xi_{Instrument_j} + \xi_{Lot \times Instrument_{ij}}$$

wherein α, β, γ, and ξ each denote contributions to the respective parameters a, b, c, and d and the respective subscripts denote the source of the contributions.

39. The method of claim 25, wherein the model is a four-parameter logistic model and the at least one probability density includes a logarithm of a sum of a lot-specific density contribution and an instrument-specific density contribution.

\* \* \* \* \*